United States Patent
Kidwell

(10) Patent No.: US 8,440,062 B2
(45) Date of Patent: May 14, 2013

(54) MULTIPARAMETER SYSTEM FOR ENVIRONMENTAL MONITORING

(75) Inventor: David A Kidwell, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1005 days.

(21) Appl. No.: 12/402,271

(22) Filed: Mar. 11, 2009

(65) Prior Publication Data

US 2009/0173629 A1  Jul. 9, 2009

Related U.S. Application Data

(63) Continuation-in-part of application No. 10/833,636, filed on Apr. 26, 2004, now Pat. No. 7,618,523, which is a continuation of application No. 10/237,074, filed on Sep. 9, 2002, now Pat. No. 6,780,307, application No. 12/402,271, which is a continuation of application No. 11/009,849, filed on Dec. 3, 2004, now abandoned.

(60) Provisional application No. 60/328,423, filed on Oct. 12, 2001, provisional application No. 60/526,284, filed on Dec. 3, 2003.

(51) Int. Cl.
*G01N 27/403* (2006.01)

(52) U.S. Cl.
USPC ............... 204/435; 422/82.01; 422/82.02; 422/82.03; 422/82.05

(58) Field of Classification Search ............ 204/435, 204/416–418, 400; 422/82.01–82.05
See application file for complete search history.

(56) References Cited

U.S. PATENT DOCUMENTS

| | | | |
|---|---|---|---|
| 4,189,367 A | 2/1980 | Connery et al. | |
| 4,399,002 A | 8/1983 | Freiser et al. | |
| 4,454,007 A | 6/1984 | Pace | |
| 4,713,165 A | 12/1987 | Conover et al. | |
| 4,773,969 A | 9/1988 | Miura et al. | |
| 4,891,125 A | 1/1990 | Schultz | |
| 4,913,793 A | 4/1990 | Leonard | |
| 5,056,521 A | 10/1991 | Parsons et al. | |
| 5,180,481 A | 1/1993 | Carey | |
| 5,330,634 A | 7/1994 | Wong et al. | |
| 5,522,978 A | 6/1996 | Pace et al. | |
| 5,531,870 A | 7/1996 | Cha | |
| 5,554,339 A | 9/1996 | Cozzette et al. | |
| 5,672,256 A * | 9/1997 | Yee ........................ | 422/82.01 |
| 5,753,519 A | 5/1998 | Durst et al. | |
| 5,891,649 A | 4/1999 | Kidwell et al. | |

(Continued)

OTHER PUBLICATIONS

Charles Benbrook, "Antiobiotic Drug Use in US. Aquaculture," Feb. 2002, http://m.iatp.org/files/421_2_37397.pdf downloaded Aug. 20, 2012.*

(Continued)

*Primary Examiner* — Alex Noguerola
(74) *Attorney, Agent, or Firm* — Amy L. Ressing; Rebecca Forman

(57) ABSTRACT

A miniature, lightweight, inexpensive, environmental monitoring system containing a number of sensors that can simultaneously and continuously monitor fluorescence, absorbance, conductivity, temperature, and several ions. Sensors that monitor similar parameters can cross-check data to increase the likelihood that a problem with the water will be discovered.

7 Claims, 18 Drawing Sheets

U.S. PATENT DOCUMENTS

| | | | |
|---|---|---|---|
| 5,914,271 | A | 6/1999 | Law et al. |
| 6,033,914 | A | 3/2000 | Boyd et al. |
| 6,087,182 | A | 7/2000 | Jeng et al. |
| 6,110,338 | A | 8/2000 | Rokugawa |
| 6,165,796 | A | 12/2000 | Bell |
| 6,212,418 | B1 | 4/2001 | Even-Tov et al. |
| 6,623,698 | B2 | 9/2003 | Kuo |
| 6,780,307 | B2 * | 8/2004 | Kidwell .................... 205/792 |
| 2002/0065332 | A1 | 5/2002 | Choi et al. |
| 2002/0130069 | A1 | 9/2002 | Moskoff |
| 2003/0121779 | A1 * | 7/2003 | Kidwell ................ 204/403.01 |
| 2003/0176933 | A1 | 9/2003 | Lebel et al. |

OTHER PUBLICATIONS

USGS Fact sheet FS-027-02 Pharmaceuticals. Hormones, and Other Organic Wastewater Contaminants in U.S. Streams Jun. 2002.*

Eman M. Elnemma & Mara Wan A. Hamada, "Liquid and Poly (Vinyl Chloride) Matrix Membrane Electrodes for the Selective Determination of Cocaine in Illicit Powders," Talanta, 1992, vol. 39, No. 10, pp. 1329-1335.

L. Campanella, C. Colapicchioni, M. Tamossetti, A. Bianco & S. Dezzi, "A new ISFET device for cocaine analysis," Sensors and Actuators, 1995, vol. 24-25, pp. 188-193.

Kiyoyuki Watanabe, Kunio Okada, Hideo Oda, Ka Tsushi Furuno, Yutaka Gomita & Takashi Ka Tsu, "New cocaine-selective membrane electrode," Anal. Chim. Acta, 1995, vol. 316, pp. 371-375.

Kiyoycki Watanabe, Kunio Okada & Takashi Katsu, "Development of an Amphetamine-Selective Electrode," Jpn. J. Toxicol. Environ. Health, 1996, vol. 42, p. 33.

Saad S. M. Hassan & Eman M. Elnemma, "Amphetamine Selective Electrodes Based on Dibenzo-18-crown-6 and Dibenzo-24-crown-8 Liquid Membranes," Anal. Chern., 1989, vol. 61, pp. 2189-2192.

Kiyoyuki Watanabe, Kunio Okada, Hideo Oda & Takashi Katsu, "Development of a Portable Cocaine-Selective Electrode," Jpn. J. Toxicol. Environ. Health, 1997, vol. 43, p. 17.

L. Campanella, L. Aiello, C. Colapicchioni & M. Tomassetti, "Lidocaine and benzalkonium analysis and titration in drugs using new ISFET devices," J. Pharm. Biomed. Anal., 1998, vol. 18, pp. 117-125.

L. Campanella, C. Colapicchioni, M. Tomassetti & S. Dezzi, "Comparison of three analytical methods for cocaine analysis of illicit powders," J Pharm. Biomed. Anal., 1996, vol. 14, pp. 1047-1054.

Saad S. M. Hassan, Eman M. Elnemma & Eman H. El-Naby, "Solid-State Planar Microsensors for Selective Potentiometric Determination of Ethylrnorphine," Anal. Let., 1999, vol. 32, pp. 271-285.

Eman M. Elnemma & M. A. Hamada, "Plastic Membrane Electrodes for the Potentiometric Determination of Codeine in Pharmaceutical Preparations," Mikrochirn Acta, 1997, vol. 126, pp. 147-151.

Larry Cunningham & Henry Freiser, "Ion-Selective Electrodes for Basic Drugs," Anal. Chim. Acta., 1982, vol. 139, pp. 97-103.

Charles R. Martin & Henry Freiser, "Ion-Selective Electrode for the Determination of Phencyclidine," Anal. Chern., 1980, vol. 52, pp. 1772-1774.

Gary D. Carmack & Henry Freiser, "Assay of Phenobarbital with an Ion-Selective Electrode," Anal. Chern., 1977, vol. 49, No. 11, pp. 1577-1579.

Vasile V. Cosofret & Richard P. Buck, "Recent Advances in Phannaceutical Analysis with Potentiometric Membrane Sensors," Critical Reviews in Analytical Chemistry, 1993, vol. 24, pp. I-58.

Kiyoyuki Watanabe, Kunio Okada, Hideo Oda & Takashi Katsu, "Development of a portable cocaine-selective electrode," Bunseki Kagaku, 1997, vol. 46, No. 12, pp. 1019-1023.

Sebojka Komorsky-Lovric, Iva Galic & Rahela Penovski, "Voltammetric Determination of Cocaine Microparticles" Electroanalysis, 1999, vol. 11, No. 2, pp. 120-123.

T. c. W. Yeow, M. R. Haskard, D. E. Mulcahy, H. I. Se~ & D. H. Kwon, "A very large integrated pH-ISFET sensor array chip compatible with standard CMOS processes," Sensors and Actuators, 1997, vol. 44, pp. 434-440.

Hyuk Jin Lee, Uk Sun Hong, Dong Kwon Lee, Jae Ho Shin, Hakhyun Nam & Geun Sig Cha, "Solvent-Processible Polymer Membrane-Based Liquid Junction-Free Reference Electrode," Anal. Chern., 1998, 70, 3377-3383.

English language translation of JP 01292246, patent published on Nov. 24, 1989.

English language translation of NL 8602668, patent published May 16, 1988.

Derwent abstract of Kamahori et al. Pub-No. JP 01292246 A, Nov. 24, 1989.

JPO abstract of Kamahori et al. Pat-No. JP 401292246 A, Nov. 24, 1989.

Derwent abstract of and figure from Schreurs et al. NL 8602668A, May 16, 1988.

Shoukry, Adel ("Use of Plastic Membrane Ion-Selective Electrodes for the Analysis of Drug Substances," Scientific Papers of the University of Pardubice, Series A, Faculty of Chemical Technology, 1(1995).

JPO abstract of Sugano et al. (JP 57-199950 A).

Caplus abstract of Kidwell ("Analysis of cocaine, heroin, and their metabolites in saliva," Report (1990), NRL-MR-6678; Order No. AD-A224173, 17 pp. Avail.: NTIS From: Gov. Rep. Announce. Index (U.S.) 1990, 90(22), Abstr. No. 058,069).

N. Papadopoulos et al., "A computer-controlled bipolar pulse conductivity apparatus," J. Chemical Education, 78 (2), 245-246, Feb. 2001.

R. T. daRocha et al., "A low-cost and high-performance conductivity meter," J. Chemical Education, 74 (5), 572-574, May 1997.

B. R. Gannong, "Hand-held conductivity meter and probe for small volumes and field work," J. Chemical Education, 77 (12), 1606-1608, Dec. 2000.

David A. Kidwell, "Measuring Copper in Seawater—An Automated Detection of Copper Binding Capacity Final Report of SERDP SEED 1266," NRL Memorandum Report 6170-03-8729, Dec. 19, 2003.

Bakker et al., How do Pulsed Amperometric Ion Sensors Work? A simple PDE Model., SIAM Review, 45, No. 2, pp. 327-344, 2003.

YSI 6500 brochure—downloaded at www.YSI.com on Mar. 12, 2009.

* cited by examiner

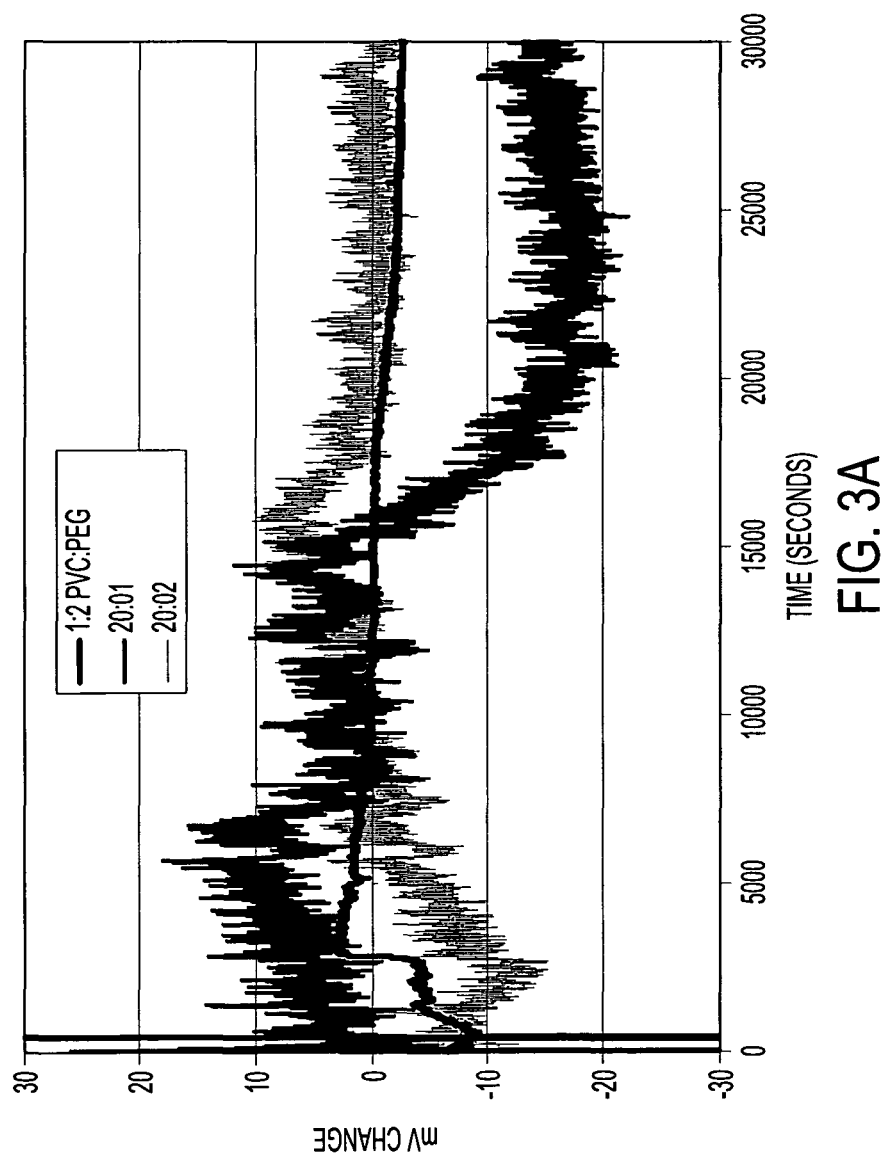

US 8,440,062 B2

MULTIPARAMETER SYSTEM FOR ENVIRONMENTAL MONITORING

PRIORITY CLAIM

This application is a Continuation-in-Part of application Ser. No. 10/833,636 filed on Apr. 26, 2004 now U.S. Pat. No. 7,618,523. application Ser. No. 10/833,636 is a Continuation of application Ser. No. 10/237,074 filed on Sep. 9, 2002 now U.S. Pat. No. 6,780,307. application Ser. No. 10/237,074 is an application claiming the benefit under 35 USC 119(e) to U.S. Provisional Application 60/328,423 filed on Oct. 12, 2001. This application is a Continuation of application Ser. No. 11/009,849 filed on Dec. 3, 2004 now abandoned. Application Ser. No. 11/009,849 claims the benefit of U.S. Provisional Application 60/526,284 filed on Dec. 3, 2003. The entirety of all of the above-referenced applications is incorporated herein in full by reference.

BACKGROUND

1. Field of the Invention

The present invention relates to environmental monitoring, and, more specifically, to a multiparameter system for environmental water quality monitoring.

2. Description of the Prior Art

Monitoring water quality is important to ensure that the water is acceptable for its intended use. Water sources are frequently contaminated and unsuitable for some uses without treatment. Often, continuous monitoring is required to ensure that the water quality remains at an acceptable level. Monitoring water quality usually requires monitoring several parameters since there are several kinds of water contamination. Additionally, monitoring several parameters helps to distinguish normal water variation from an abnormal event that may require closer scrutiny.

Current technologies for monitoring water quality provide continuous monitoring for multiple parameters. One example of a multi-parameter, water-quality monitoring system that provides continuous data is the YSI 6500 Monitoring System (www.YSI.com). However, this instrument has the disadvantages of being bulky (1.6 inch diameter, 14 inch length), heavy (1.5 pounds), expensive, and only a limited number of multiple parameters being available. In addition, the important concept of measurement of the free metal ion binding capacity of a water source is not addressed. Often, the toxicity of heavy metals in an estuary environment is not due to their absolute concentration but the concentration of the free metal ions (those not complexed to the organic matter in the water). The capacity of the water to absorb additional metal ions is related to this excess binding capacity. If low, that water body is more susceptible to pollution than a similar water body with more capacity.

SUMMARY

The aforementioned problems with the current technologies are overcome by the present invention wherein a miniature, lightweight, inexpensive, environmental monitoring system containing a number of sensors can simultaneously and continuously monitor fluorescence, absorbance, conductivity, temperature, and several ions. Moreover, in the present invention, the sensors that monitor similar parameters can cross-check the data to increase the likelihood that a problem with the water will be discovered. Additionally, the present invention is capable of performing amperometric and cyclic volumetric measurements, which can be useful for measurement of certain ions, operation of enzyme electrodes, and measurement of selective binding capacity of a water system for selected ions.

The present invention provides several advantages over the prior art. It is a miniature package (about 2.25 inches by 4 inches) as opposed to the prior art that is about 1.6 inches by 14 inches. It is lightweight, weighing only about a quarter of a pound compared to the prior art that weights about a pound and a half. Additionally, it cost effective and easy to manufacture. Moreover, the present invention can use information from sensors that monitor similar parameters to crosscheck the data. Additionally, the present invention can generate selected ions in a controlled fashion to allow measurement of the free metal binding capability of a water source.

BRIEF DESCRIPTION OF THE DRAWINGS

These and other features and advantages of the invention, as well as the invention itself, will become better understood by reference to the following detailed description, appended claims, and accompanying drawings where:

FIGS. 3a and 3b plot voltage change over time for several cast membrane formulas;

DETAILED DESCRIPTION

Figure 1A:
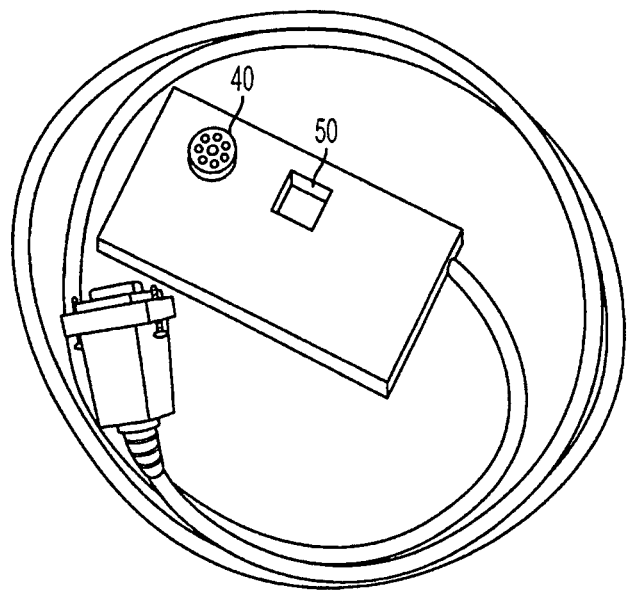
FIGS. 1a and 1b are top views of two versions of an environmental monitoring system.
Figure 1B:
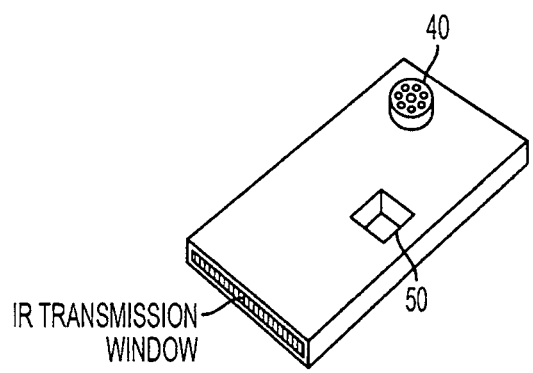

Two versions of a preferred embodiment of the environmental monitoring system of the present invention are shown in FIGS. 1a and 1b. FIG. 1a shows a direct connect version that can be used, for example, for laboratory testing and quick field sampling. FIG. 1b shows an IR version that can be put in place to take and store data for days to months. Both versions have a sensor array 40 and a well for optical measurements 50. The environmental monitoring system weighs less that a pound, and is typically about 0.25 pounds. Its width is less than four inches, and is typically about 2.25 inches; and its length is less than 6 inches, and is typically about 4 inches.

A preferred embodiment of the environmental monitoring system may have sensors for absorbance, fluorescence, conductivity, enzyme activity (metal ions via cyclic voltametry) and temperature. In addition, it will have at least one, but preferably an array of ion selective electrodes to monitor charged analytes, e.g., pH, potassium, chloride, copper, magnesium, sodium, calcium, phosphates, organophosphates, cyanide, fluoride etc. A sensing electrode of the present invention may measure current and/or oxidation-reduction potential and may be one or more of the above type of electrodes. The selectivity of the ion selective electrodes is governed by the choice of carrier molecule for wire coated and liquid filled electrodes or the choice of ionic crystal for solid-state electrodes. These systems are well known in the art. A cast membrane reference electrode is used with the ion selective electrodes.

In a further preferred embodiment, the sensors are monitored continuously, once per second for up to 30 days. The data may be stored on-board the environmental monitoring system or sent remotely, for example through a RS232 or IR link. The environmental monitoring system may be field programmable to allow for greater flexibility.

The environmental monitoring system uses several orthogonal sensors, which (1) increase the likelihood that an unusual event will be discovered since each sensor measures different aspects of the sample and (2) allow for cross-checking the data for sensors that monitor similar aspects of the water. For example, the ion selective electrodes monitor specific ions, whereas the conductivity sensor monitors all ionic species in solution. Because the ion selective electrodes do not measure all ionic species, some ionic materials may be missed. On the other hand, if the calculated conductivity from the ion selective electrodes matches that from the conductivity sensor, one can have greater confidence that some additional ionic species was not present in substantial concentrations. An additional example is the absorbance and fluorescence detector combination. The absorbance detector responds to both particles and dissolved species in solution. If a wavelength is chosen for the excitation source such that it is not entirely blocked by the filter in front of the fluorescent detector, then the fluorescent detector can act as a light scattering detector as well as a fluorescent detector. In this mode, particles are detected because they scatter the incident light, whereas dissolved materials do not. Additionally, by varying the wavelength of the incident light (and angles), some indication of the sizes and distribution of sizes of the particles can be estimated.

The environmental monitoring system has internal data storage capabilities and can take data independent of a computer. Currently, the system has about 128 megabytes of memory, which allows for greater than 30 days storage of data collected continuously, once per second for 16 parameters. Three ways for the environmental monitoring system to communicate to another device are direct connect, IR connect, and radio waves. For design considerations, connecting with IR connect and radio waves are easier to waterproof.

Ion Selective Electrodes

The present invention uses ion selective electrodes, which were described in related applications for a drug monitoring system: U.S. Pat. No. 6,780,307 to Kidwell, Aug. 24, 2004; Provisional application No. 60/328,423 filed on Oct. 12, 2001 by Kidwell; and U.S. application Ser. No. 10/833,636 filed on Apr. 26, 2004 by Kidwell, the entire contents of each is incorporated herein by reference. Ion selective electrodes can contain different types of sensors. In the present invention, the term ion selective electrode is considered to include liquid membrane types of ion selective electrodes, polymer membrane types of ion selective electrodes, solid-state ion-selective electrodes, and ion-selective, field-effect transistors.

An ion selective electrode, which is equivalent to a battery, contains two poles where electrons originate and conclude to complete an electrical circuit: a sensing electrode and a reference electrode. For membrane-type electrodes, such as liquid filled or wire coated electrodes, a semi-permeable membrane separates the two poles. Ions are carried across the semi-permeable membrane with a selective transporter molecule—the driving force being a concentration gradient on either side of the membrane. Because the transport molecule carries only one part of the ion pair, a charge build-up occurs inside the ion selective electrode solution. This charge build-up generates a voltage that can be measured and resists further diffusion of analyte cations. With higher concentrations of analyte, the voltage will be higher.

Figure 2:
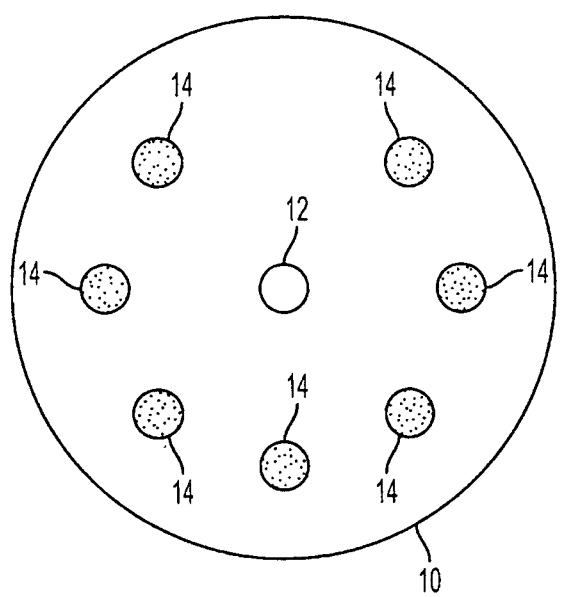
FIG. 2 is a top view of an ion selective electrode.

An environmental monitoring system (EMS) in accordance with a preferred embodiment of the present invention generally includes a cast membrane reference electrode, at least one but preferably an array of sensing electrodes each with a semi-permeable ion selective membrane. The reference electrode and sensing electrodes are typically housed in a plastic rod, preferably a PVC rod. Other materials, such as Tygon® tubing, can be used for the electrode body. Holes can be drilled into the rod for the electrodes. As shown in FIG. 2, a hole is drilled in the center of the rod 10 for the reference electrode 12, and at least one but preferably 6-7 holes are drilled in a circular format around the perimeter of the rod for the sensing electrodes 14. Alternatively, the holes for the reference electrode and sensing electrodes can be drilled anywhere in the rod, and any number of holes can be drilled for the sensing electrodes depending on how many sensing electrodes are desired. The rod used to house the electrodes can be any size, and it can be planar. Alternatively, the sensing electrodes may be individual electrodes of miniature size rather than an array. This format has the disadvantage of being less compact, but has the advantage of being able to replace ion selective electrodes that become inoperative or to build a group of electrodes for a specific application.

Reference Electrode

To allow accurate readings in a widely varying media, most reference electrodes use a concentrated salt solution as an inner filling solution and a porous plug to make electrical contact with the test solution. The porous plug acts as a small leak for the inner salt solution. Typical porous materials are porous glass frits, cracked glass, fiber, gels (which tend to dry out and thereby fail), or a small hole (which requires frequent refilling of the reference electrode). Using these types of porous materials makes manufacturing the ion selective electrode difficult because of the manual placement of the plug or the reproducible preparation of the hole. Furthermore, porous plugs can bio-foul causing the ion selective electrode to fail. To avoid these problems and ease manufacturing, the present invention uses a porous membrane that can be cast into place, thereby allowing easy assembly. Additionally, the membrane performance does not degrade when allowed to "dry" out. After being left unprotected at room temperature, the ion selective electrode provides a stable signal within a few minutes of being placed back into water.

Using a castable reference electrode allows water-soluble (hydrophilic) species, such as polyethylene glycol (PEG), non-ionic surfactants, ethylene glycol and higher polymers, and glycerol, to form immiscible solutions in host (hydrophobic) species, such as polyvinyl chloride (PVC), epoxy, polyvinyl butyral-co-vinyl-alcohol-co-vinyl acetate. The hydrophobic species form the membrane and provide support. The hydrophilic species may either be leached from the hydrophobic species forming pores through which ions may flow or remain in the hydrophobic species and act as ion carriers. Examples of hydrophilic species include polyethylene glycol, ethylene glycol and higher polymers, glycerol, and polypropylene glycol in a wide variety of molecular weights, but those with lower molecular weights work better.

Figure 3B:
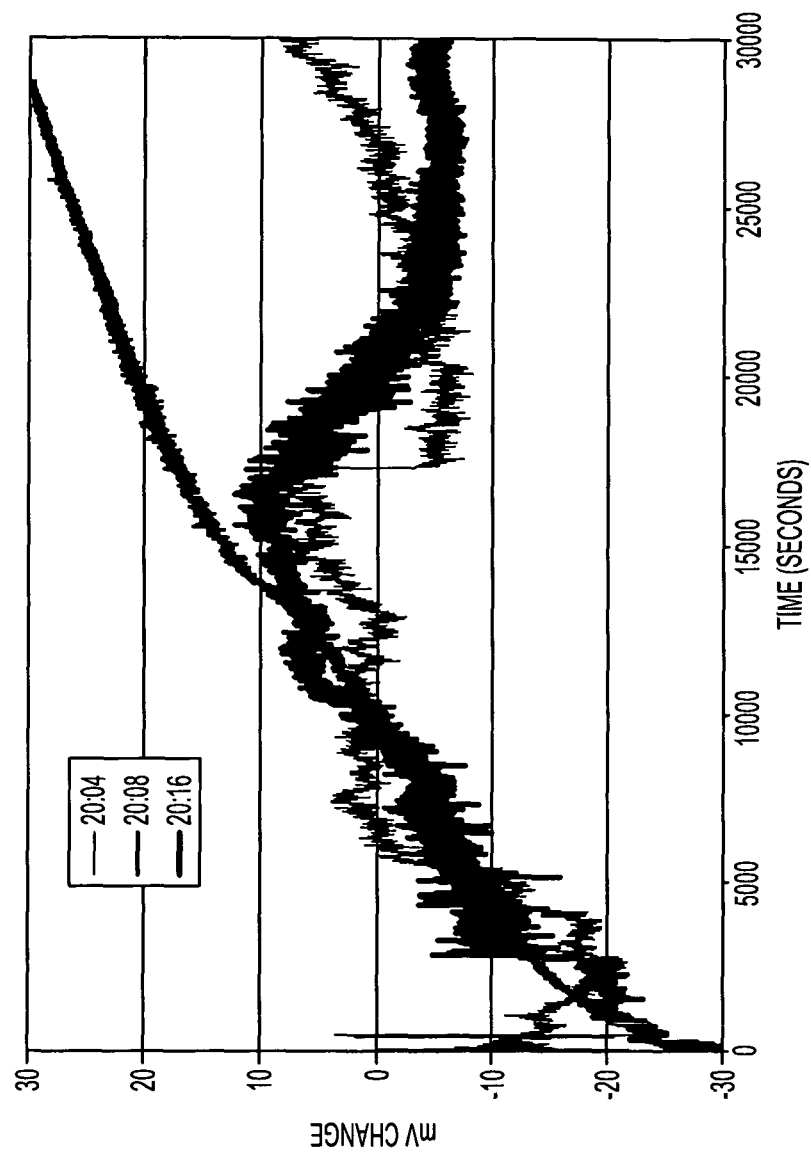

FIGS. 3a and 3b compare a cast membrane electrode using the standard formula of 1:2 PVC:PEG1450 with cast electrodes made from various ratios of PVC and Triton X100. The potential of the reference electrodes were monitored vs. a commercial reference electrode as the counter electrode. The 1:2 PVC:PEG1450 cast membrane reference had a lower noise and lower drift than the alternative formulation. However, the 20:16 PVC:Triton X100 (20 mg PVC:16 mg Triton X100 dissolved in THF) reference had comparable noise and stability.

Figure 4A:
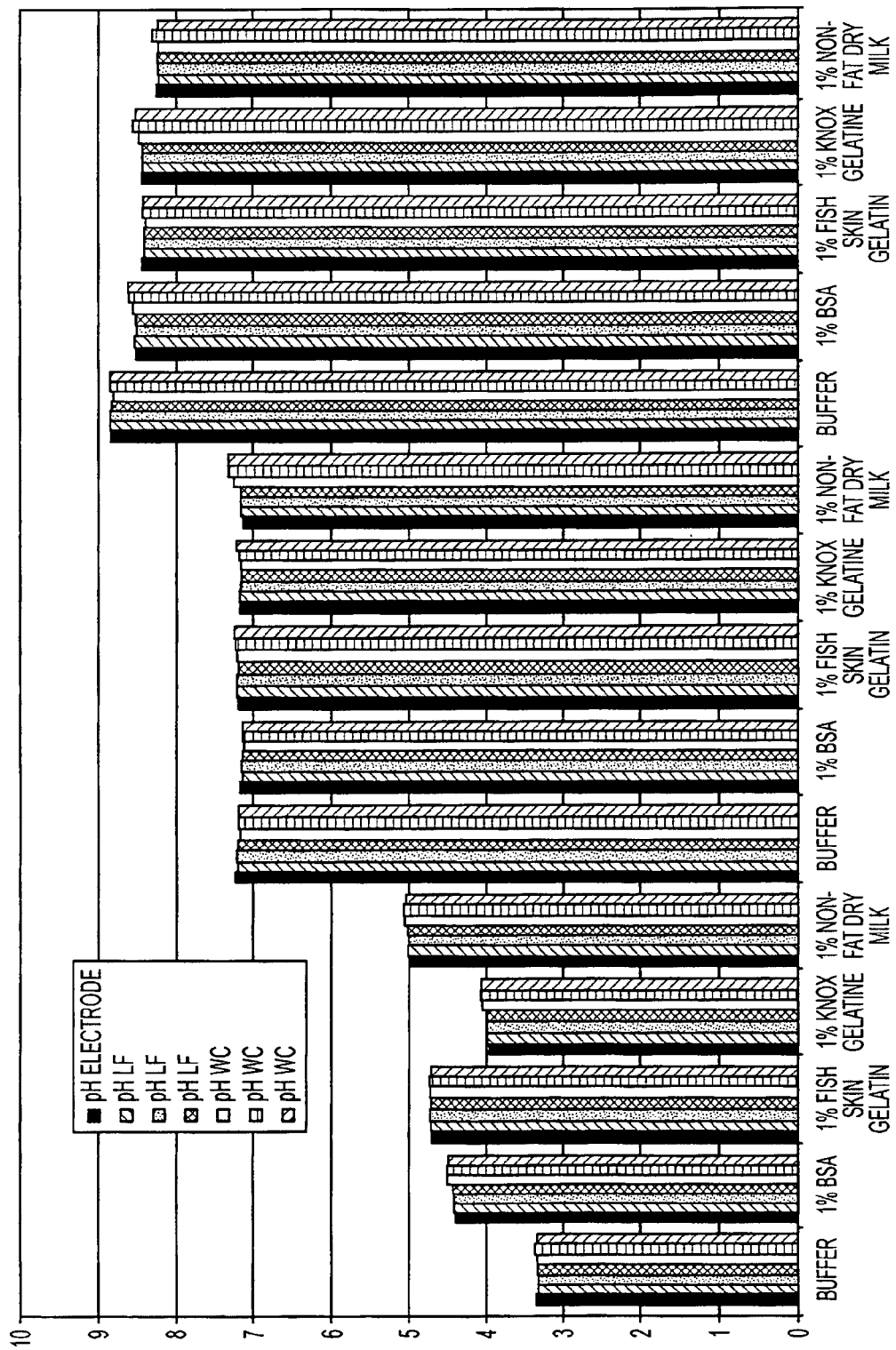
FIGS. 4a and 4b compare the cast membrane reference electrode to a commercial reference electrode.
Figure 4B:
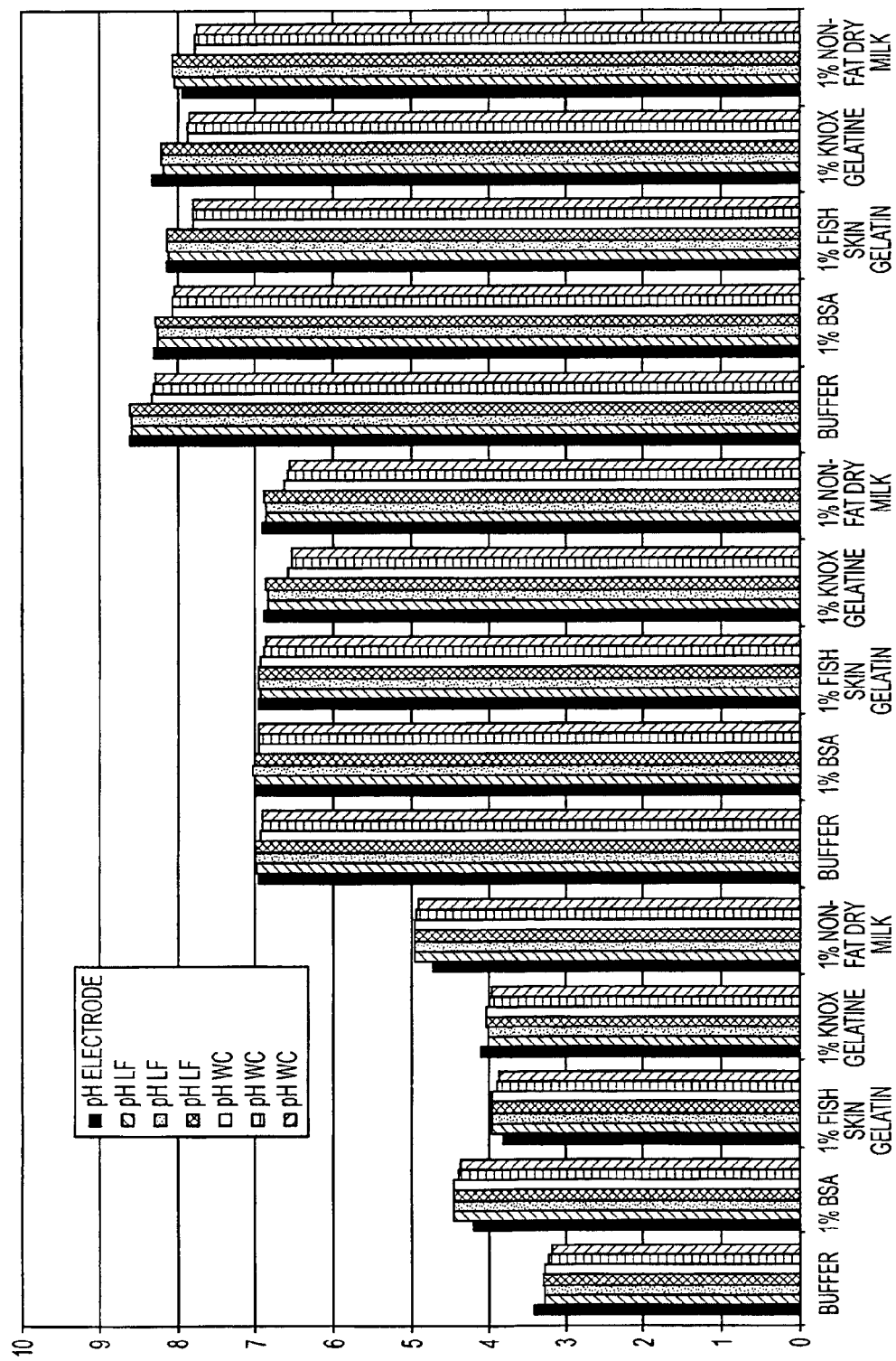

The cast reference electrodes also had reduced bio-fouling tendencies. FIGS. 4a and 4b compare the 1:2 PVC:PEG1450 cast reference electrode to a commercial reference electrode using a porous polymer frit (Orion pH probe, gel-filled) in five different solutions at three difference pHs. Three types of pH electrodes were tested: (1) A commercial glass electrode as a pH sensor—glass electrodes being known to be susceptible to protein fouling (designated as pH electrode in FIGS. 4a and 4b). (2) A membrane-type pH sensor with the membrane coated on a copper wire (in FIGS. 4a and 4b, WC means wire coated). And (3) a membrane-type pH sensor with an internal liquid filling (in FIGS. 4a and 4b, LF means liquid filled). FIG. 4a shows electrode arrays with 3 types of ion selective electrodes tested with various protein solutions at various pHs using a commercial reference electrode. FIG. 4b shows electrode arrays with 3 types of ion selective electrodes tested with various protein solutions at various pHs using cast membrane reference electrode. The cast reference electrode showed similar performance in the various media yet had a lower leakage rate of the internal filling electrolyte.

To form the reference electrode, a membrane solution is used that consists of a hydrophobic species, preferably PVC, and a hydrophilic species, preferably polyethylene glycol with molecular weight of approximately 1450, in varying ratios, preferably 1:2 parts by weight of PVC to polyethylene glycol in a compatible solvent, preferably tetrahydrofuran. Approximately 5 µl of the membrane solution at room temperature is placed at the bottom end of the center hole drilled in the PVC rod, and surface tension keeps the liquid completely across the hole. The rod is held vertically for a few minutes and is allowed to completely dry to form a semipermeable membrane. Preferably the solution is allowed to dry overnight at room temperature, or alternatively it can dry for approximately 30 minutes at room temperature and then 30 minutes at 60° C. The membrane should be translucent and should completely cover the hole. The closer the membrane is to the end of the rod, the better the electrode performance. Membranes that are recessed slightly can have pockets where mixing with the bulk solution is slow and thereby result in poorer electrode performance.

The electrode is filled from the top end of the drill hole with a salt solution, such as $NaNO_3$, $KCl$, $Na_2SO_4$, $NaF$, or $LiF$ but preferably $KCl$, by using a gel filling pipette tip placed inside the chamber and slowly withdrawing the tip as liquid is dispensed. Air bubbles should be avoided. A wire, preferably a silver wire coated with AgCl, is placed in the top at least halfway down in the filling solution and sealed, preferably with epoxy. The wire can have a very short piece of heat-shrunk tubing that acts as a sleeve. This tubing both reduces the sealing distance required of the epoxy and helps center the silver wire in the reference body. The silver wire may be bent into a sharp S shape at the top of the electrode to help allow the epoxy hold the wire in place. The AgCl coated silver wire is either made by oxidizing silver electrically in a KCl solution or more preferably by using a $FeCl_3$ solution used to etch printed circuit boards as sold by GC Thorsen, Inc., Rockford, Ill.

Sensing Electrodes

The sensing electrodes are prepared in a similar way as the reference electrode. The membrane solution for the sensing electrode consists of a hydrophobic species, such as PVC, and at least one ionophore that is selective for the ion to be tested. Alternatively, the sensing electrode can be solid state—one example is a pressed pellet of silver chloride being selective for chloride ions.

Baseline or zero drift can be handled in four ways: (1) Calibrate the sensing electrodes of the ion selective electrode before each use with a distilled water bank and use that reading to zero the calibration curve. This assumes that the slope of the calibration line does not change with aging of the sensing electrode. (2) Use a non-specific sensor on the array to zero the system. The sensor would be selective for materials that would not likely occur in the environment being monitored. For example, quaternary ammonium compounds are not likely to be present in a natural water stream. Therefore, a sensor selective for these materials can be used to zero the system. This has the advantage of allowing correction of the values on a continuous basis. It has the disadvantage of not correcting for any slope changes due to aging of the electrodes. (3) Calibrate the sensing electrodes before each use with calibrants at two concentrations. This corrects for both baseline drift and any slope change in the electrode and is the preferred method for accurate concentration measurements. (4) Calibrate the sensors before placement in the environment and after removal. Assume that the slope degradation and zero offsets are linear with time (or have a similar degradation pattern to another sensor array) and back correct all the measurements.

The Absorbance and Fluorometer Sensors

In a preferred embodiment, the absorbance and fluorescence sensors comprise a matched pair in a T arrangement. The cell is machined in to the plastic body and has about a one centimeter path length. The light output from the LED is measured using a Texas Instrument T1254 and the fluorescence is measured using a T1255. Both integrated circuits output a voltage proportional to the input light level and are digitized with two separate A/D converters. The algorithm for detecting the light levels is as follows:

1. Turn-on the two detectors
2. Delay for stabilization
3. Read background fluorescent light level sensor
4. Turn on LED
5. Read fluorescence and absorbance sensors and average 16 times
6. Determine if background light level is too high
7. If sufficiently low, subtract from measured level
8. Report values The absorbance sensor both monitors the output of the LED as well as measures the absorbance of the solution in the cell. Because there is no independent measurement of light output, if very large concentrations of fluorescent materials are present or they are present in conjunction with other absorbent materials, both sensors will respond. Therefore, a ratio of the sensors is not used and only the absolute value of each sensor is measured. The absorbance level does have some value as the battery voltage is measured independently of the light output and can be used to estimate if the light output is stable.

An additional light sensor could be added to measure the LED emission from the back of the LED (and thereby monitor light output) at a cost of one additional A/D converter, then not available for other measurements. Because the LED is toggled on for only 1 ms, to save power, a light sensor such as the Texas Instruments T1252 (which outputs a square wave proportional to light intensity) would not be practical because the counting time would be too short. The T1252 would save one A/D converter. Thus a trade-off was made between additional sensors, power, and signal reliability in this design.

For fluorescent measurements, a filter is used to remove the excitation light. Often these filters are interference filters. Small interference filters are no longer being manufactured but can be purchased on a custom basis. Nevertheless, their high cost (>$10 each) can be prohibitive for some applications. Kodak Wratten filters were also considered but these gelatin filters are not environmentally rugged, are difficult to mount, and offer little advantage over the solution ultimately used. To reduce cost and provide more convenient assembly, paint-on filters were employed using stain-glass stains. The absorbance spectra for various stain glass paints are given in FIG. 5. Additionally, the emission spectra for various LEDs is shown in FIG. 6. Selection of the proper emission and filter sets for a given fluorescent analyte can be easily made by referring to these figures.

Figure 7:
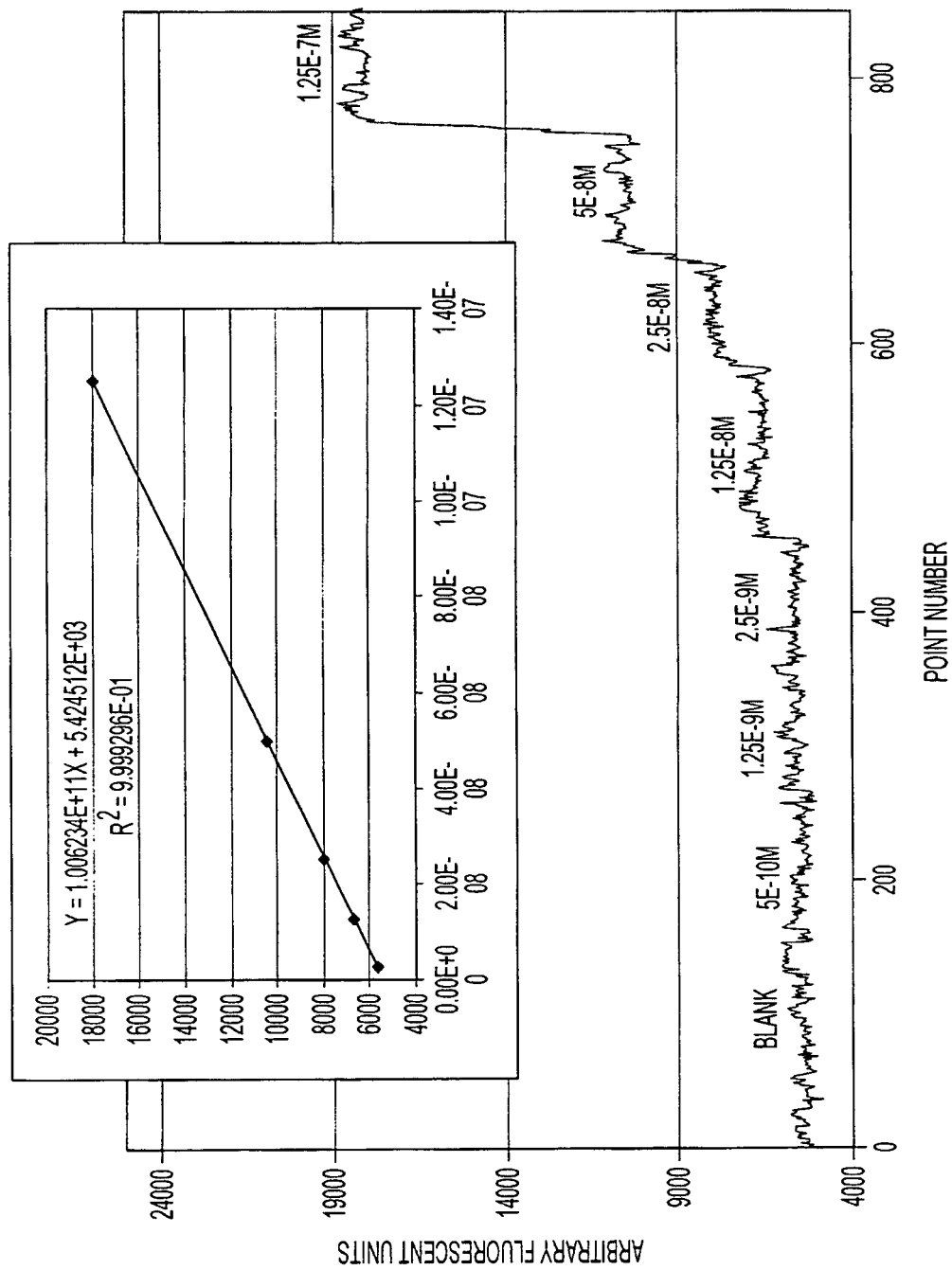
FIG. 7 shows the response of the fluorometer.

The response of the fluorometer to introduction of Fluorescein or Rhodamine 6G into the flowing system is shown in FIG. 7. Fluorescein at 1.25E-8M could be detected. Interestingly, Rhodamine 6G gave a similar detection limit of 2E-8M even though the excitation source was not optimized. One of the issues with fluorescence is reduction in scattering of the excitation light source. Part of this reduction comes from the T nature of the sample well. However, in highly scattering solutions, a signal will be recorded because the excitation source is not monochromatic and the filter set, made from stain-glass paint does not possess a sharp cut-off. The problems with scattering can be seen in FIG. 8, where a non-fluorescent scatterer was introduced into the flowing system. A scatterer, with an absorbance of 0.17, will produce a fluorescent signal corresponding to 9.4E-8M of Fluorescein. In contrast to a scatterer, an absorber will reduce the fluorescent signal because it absorbs the excitation light, some of which makes it through the excitation filter (see FIG. 9).

Figure 5:
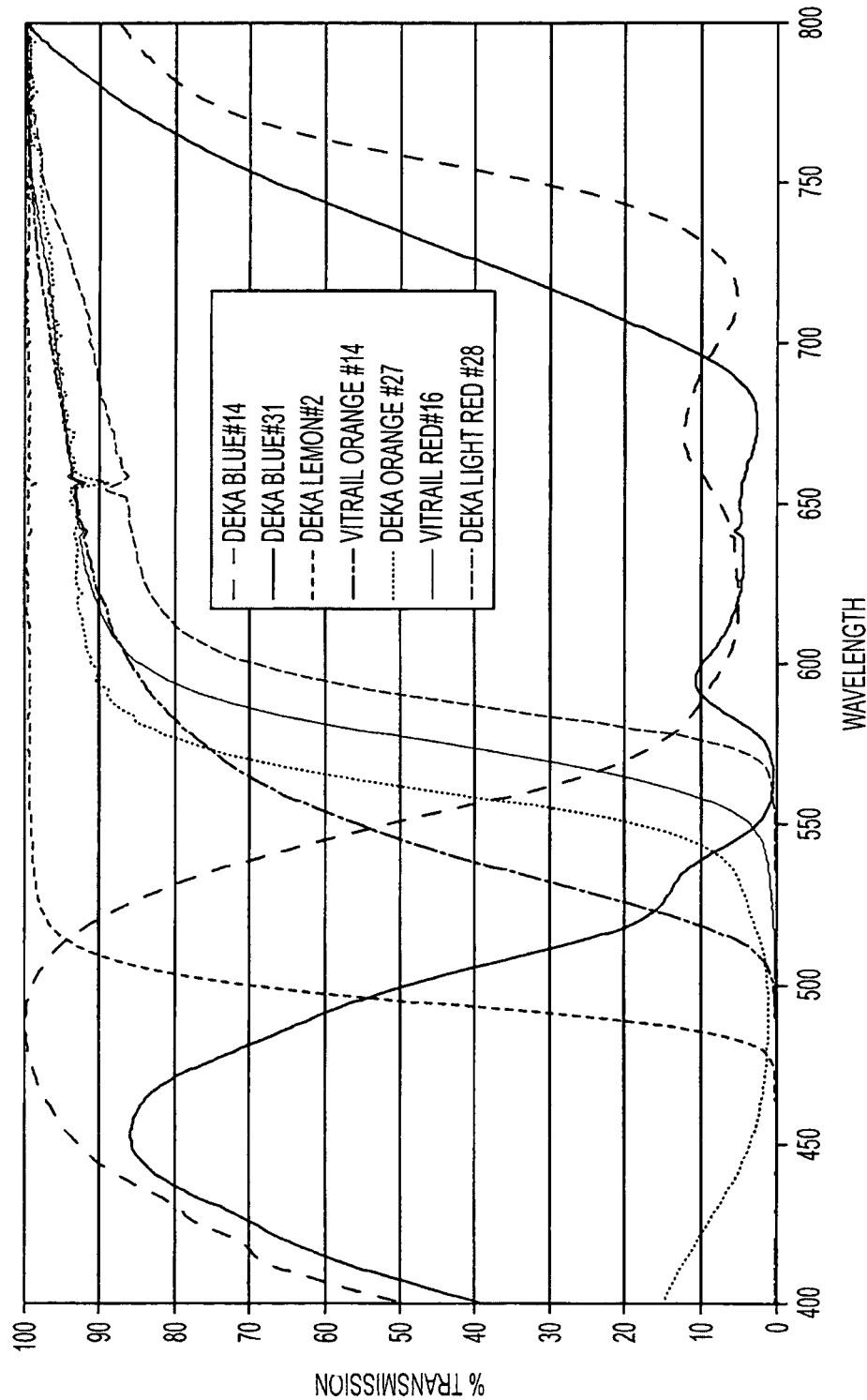
FIG. 5 shows the absorbance spectra for several stain glass paints.
Figure 6:
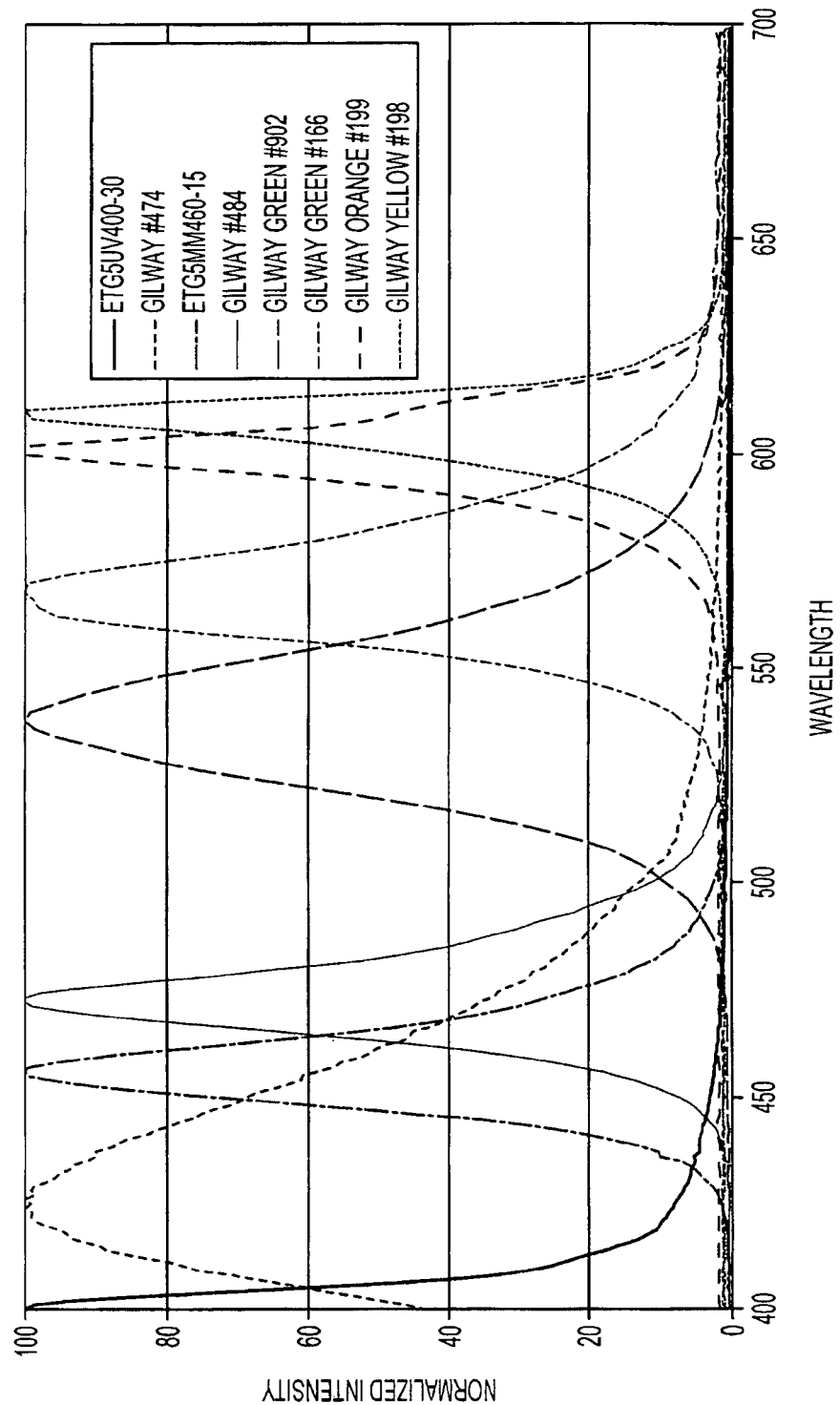
FIG. 6 shows the emission spectra for several LED light sources.

FIG. 5 shows selected absorbance spectra for various stain glass paints. Only the transparent paints are shown. The translucent paints scatter light too much to be of use in this application. The paints were painted on transparency film, the film cut to size, and the absorbance measured in a HP 8451A photodiode spectrophotometer. The absorbance values were converted to % transmission, normalized and plotted.

FIG. 6 shows elected emission spectra for various LED light sources. The spectra were recorded on a SLM 8000 fluorometer and are normalized. Overdriving an LED will broaden the emission spectra. Because the filtration provided by the stain-glass paints is not as sharp as an interference filter, a trade-off must be made between light intensity and background from the excitation leakage. Only bright LED sources were chosen for testing. Note that the typical specification of emission width at half maximum does not tell the complete story as some LEDs (such as Gilway #474) have very long emission tails. There are some commercially available optically filtered LEDs, such as one sold by UDT Sensors, Inc., Hawthorne, Calif.

FIG. 7 shows the results of detection of fluorescein with the fluorescent sensor. Fluorescein dye was introduced into the water bath at increasing concentrations. The inset shows that the response for higher concentrations is linear. The LOD for fluorescein was about 7.7E-9M. Rhodamine 6G gave a similar LOD of 2E-8M even though the excitation source and emission filter were not optimized.

Figure 8A:
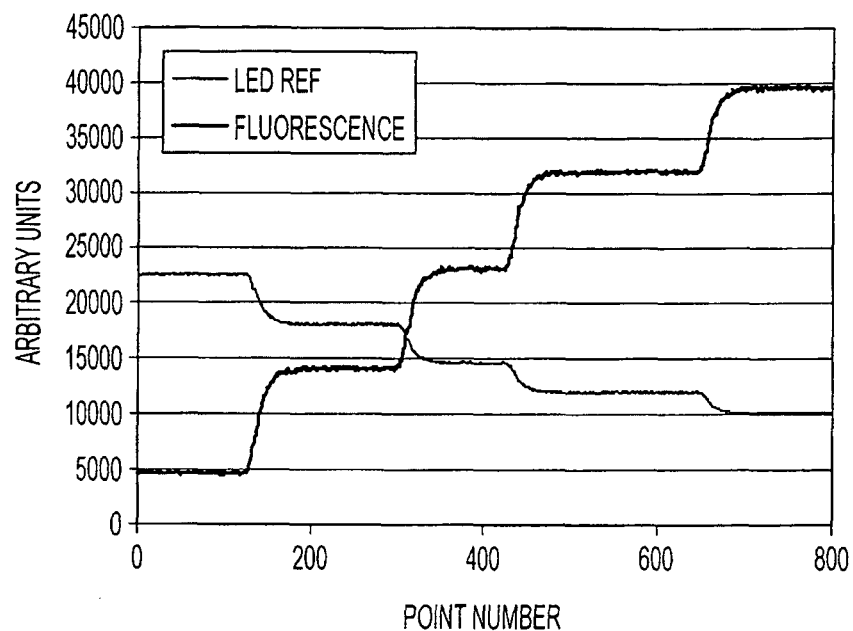
FIG. 8 shows the output of the fluorescent sensor with a scatter or an absorber.
Figure 8B:
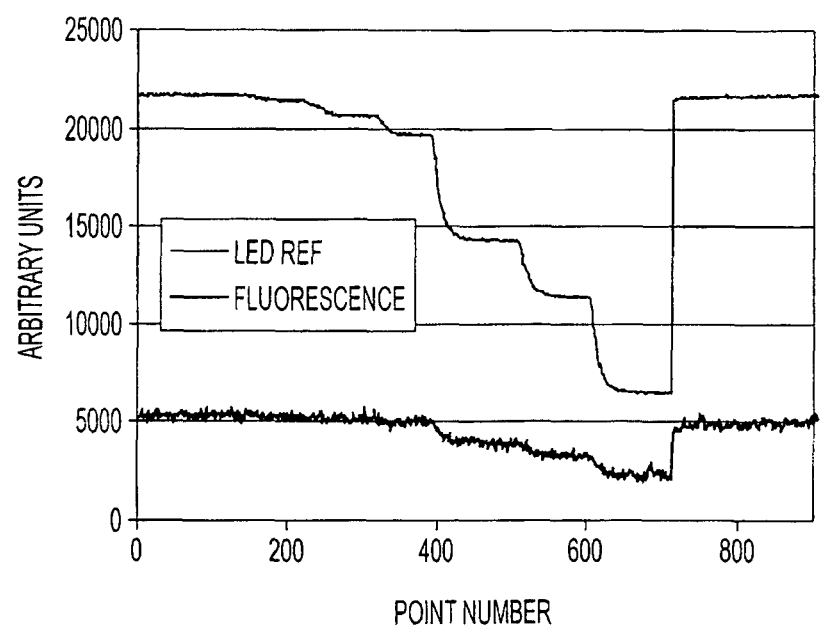

FIG. 8 shows the output of the fluorescent sensor with a scatter (a) or an absorber (b). Increasing amounts of coffee creamer (in 250 mg/L) increments were added to the flowing system. Samples were also taken for analysis on a HP 8451A diode array UV-Vis spectrometer to measure the absorbance of the solution at 470 nM. Coffee creamer is just barely fluorescent when measured in a SLM8000 fluorometer and therefore acts as a pure scatterer. The absorber was methyl orange in increasing amounts starting at point 100.

Figure 9A:
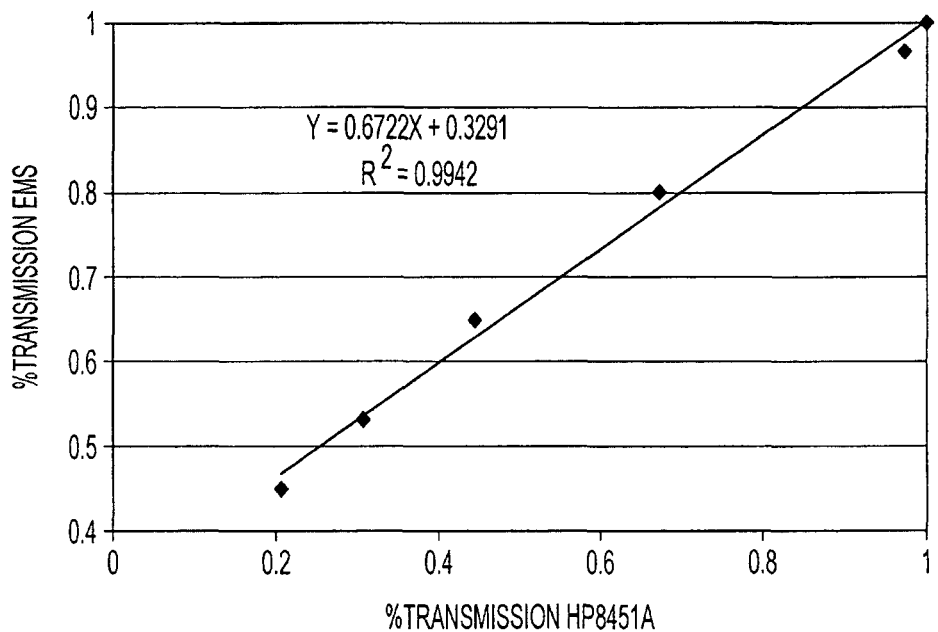
FIG. 9 compares the percent transmitted measured by the present invention with that of a diode array UV-Vis spectrometer.
Figure 9B:
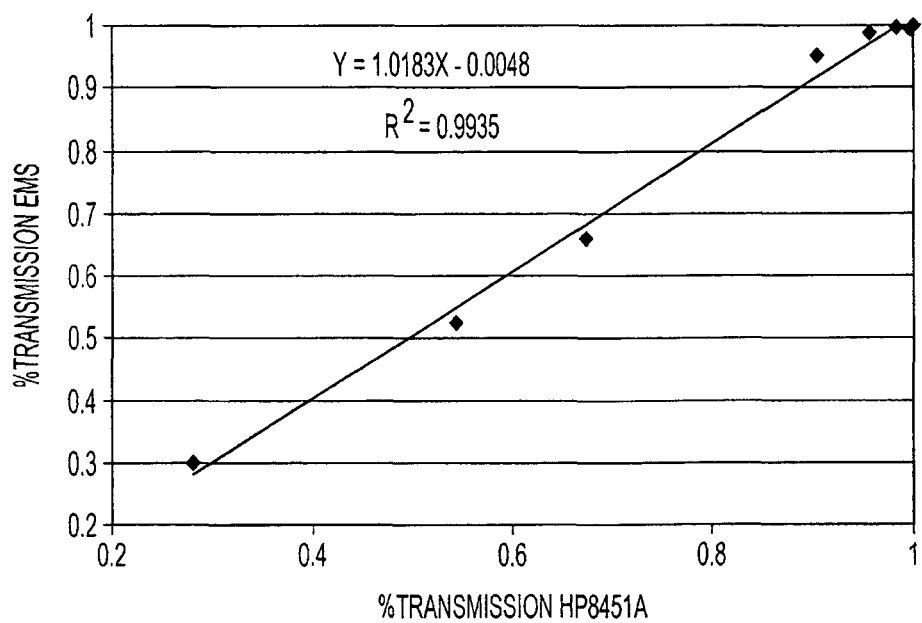

FIG. 9 shows a comparison of the % transmittance measured with the environmental monitoring system to that measured with the HP 8451A diode array UV-Vis spectrometer. Output of the fluorescent sensor with a scatter (a) or an absorber (b). Increasing amounts of coffee creamer (in 250 mg/L) increments were added to the flowing system for A. Samples were also taken for analysis on a HP 8451A diode array UV-Vis spectrometer to measure the absorbance of the solution at 470 nm. The absorber was methyl orange in increasing amounts starting at point 100 in B. The % Transmittance was measured at 470 nm with the HP 8451A.

The Conductivity Sensor

The conductivity sensor is based on conductivity measuring techniques described in the literature. See, e.g., N. Papadopoulos et al., "A computer-controlled bipolar pulse conductivity apparatus," J. Chemical Education, 78 (2), 245-246, February 2001; R. T. daRocha et al., "A low-cost and high-performance conductivity meter," J. Chemical Education, 74 (5), 572-574, May 1997; and B. R. Gannong, "Hand-held conductivity meter and probe for small volumes and field work," J. Chemical Education, 77 (12), 1606-1608, December 2000, the entire contents of each are incorporated herein by reference. However, these concepts were greatly modified to allow for unipolar (single battery voltage) operation, the ability to operate over an expanded range without switching the load resistors, and fewer (two cheap resistors) and lower power components. The principle of operation can be understood by referring to FIG. 10. For construction of the cell, two platinum wires (0.015") are place inside the optical cell approximately 1 cm apart with just the ends in contact with the test solution. The algorithm to measure conductivity is as follows:

1. Ground Cond3
2. Float Cond1
3. V+ to Cond2
4. Measure $V_{in}$ with A/D7
5. Float Cond2
6. V+ to Cond1
7. Measure $V_{cell}$ with A/D7
8. Reverse polarize cell by:
9. Ground COND1
10. V+on Cond3 for a few microseconds
11. Ground Cond1, Cond2, and Cond3 for 1 ms to short the cell
12. Measure zero value for determining offset of A/D7 (assume A/D linear to full scale)
13. Repeat all steps 16 times, summing results to initial result and subtracting zero value
14. Float Cond1, Cond2, and Cond3

The cell resistance is calculated by:

$$R_{cell} = V_{in} * Rt/V_{cell} - Rt$$

$$Rt = R1 + R2 = 10.5K$$

The cell conductivity is calculated by:

$$\text{Conductivity(uncalibrated)} = 1/R_{cell}$$

To avoid shorting the ion selective electrodes, which are in electrical contact with the conductivity cell, the reference electrode must be floated during the reading of the conductivity cell. Otherwise, a high current is pulled from the reference electrode to the conductivity cell electrodes, which quickly changes the value of the reference electrode. Likewise, the conductivity cell electrodes must be floated during the reading of the ion selective electrodes to avoid excessive current paths. The floating of the various contact points is accomplished using the on-chip hardware in the TIMSP430-F149 (for the conductivity cell) or the on-chip hardware in the Maxim 5722 D/A, which drives the reference electrode. Unfortunately, both the high impedance outputs of integrated circuits are not specified as to their isolation values and have leakage current typical values of 18-50 nA. This moderate current places strain on the reference electrode, especially in highly conductive water, such as sea water and therefore, will reduce the lifetime of the sensor package.

Figure 10:
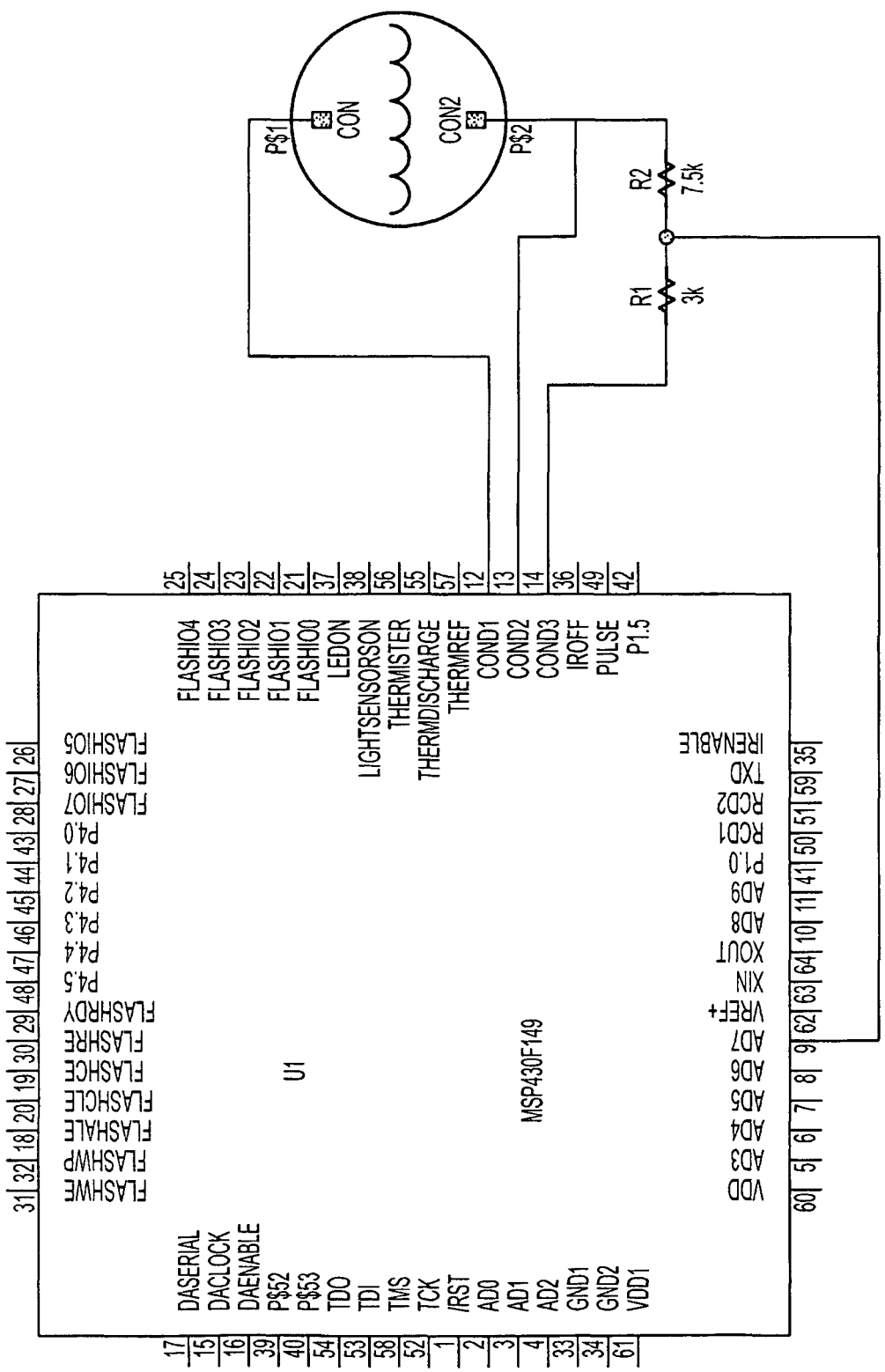
FIG. 10 is a schematic of a conductivity measuring cell.

The voltage divider constructed from R1 and R2 in FIG. 10, brings the measurement voltage within the range of the A/D (0-2.5V). The results are summed 16 times and are guaranteed to be in the range of 16 bits because the A/D is only 12 bits. Summing data provides an average for reduce electrical noise. A sum of 16 is always used regardless of the average settings for obtaining the ion selective electrode data. Two assumptions are made: (1) The A/D is linear to full scale and only an offset correction need be applied. and (2) The voltage supplied by the Cond3 pin is identical to that supplied by the Cond1 pin or at least they are related. Note that the voltages supplied by these pins are a function of the supply voltage, which will vary with the battery age. However, because the calculation involves a ratio, the results are independent of supply voltage as long as the voltage is sufficient to allow conduction across the cell.

Calibration of the cell is accomplished with serial dilutions of 0.5M sodium chloride. Because the cell constant is unknown, the results must be compared to that obtained with a standard conductivity meter to obtain calibrated results. The calibrated conductivity is calculated from the least squares plot of the uncalibrated conductivity vs. standard instrumentation. It is linear below 0.25M NaCl. This approach will work well in fresh waters, which have low salt concentrations, but it will be a concern for working in natural seawater where the salt concentration is about 0.5M. Above 0.25M NaCl, the resistance of the cell is too small to measure (about 750Ω for 0.5M NaCl) with the voltage divider, and the higher current causes some electrolysis of the test solution. Therefore, the measured conductivity is lower than expected and a non-linear calibration must be used in the region above 0.5M NaCl.

Some increased accuracy can be obtained with software modifications. Currently, the A/D is read with a small charging delay to allow the A/D capacitor to charge through the cell resistance. When the cell resistance is small (due to high salt concentrations), this delay can be shortened and thereby reduce the electrolysis time. The software can be modified to make a preliminary measurement of the cell resistance and adjust the A/D charging time-based on this preliminary measurement. However, this would require slightly longer measurement time and preliminary evaluations of this scheme did not produce completely linear conductivity measurements above 0.25M NaCl. Because a polynomial curve would still be needed above 0.25M NaCl, these more complex measurements were not implemented.

An alternative design would be to use a voltage to current converter, as is normally done. However, this would require addition of a digital switch to remove the voltage to current converter when the conductivity was not being measured or selection of an operational amplifier that can be disabled. Maxim sells such switches, which are low power and high impedance, but add to the cost of the final product.

The Temperature Sensor

Figure 11:
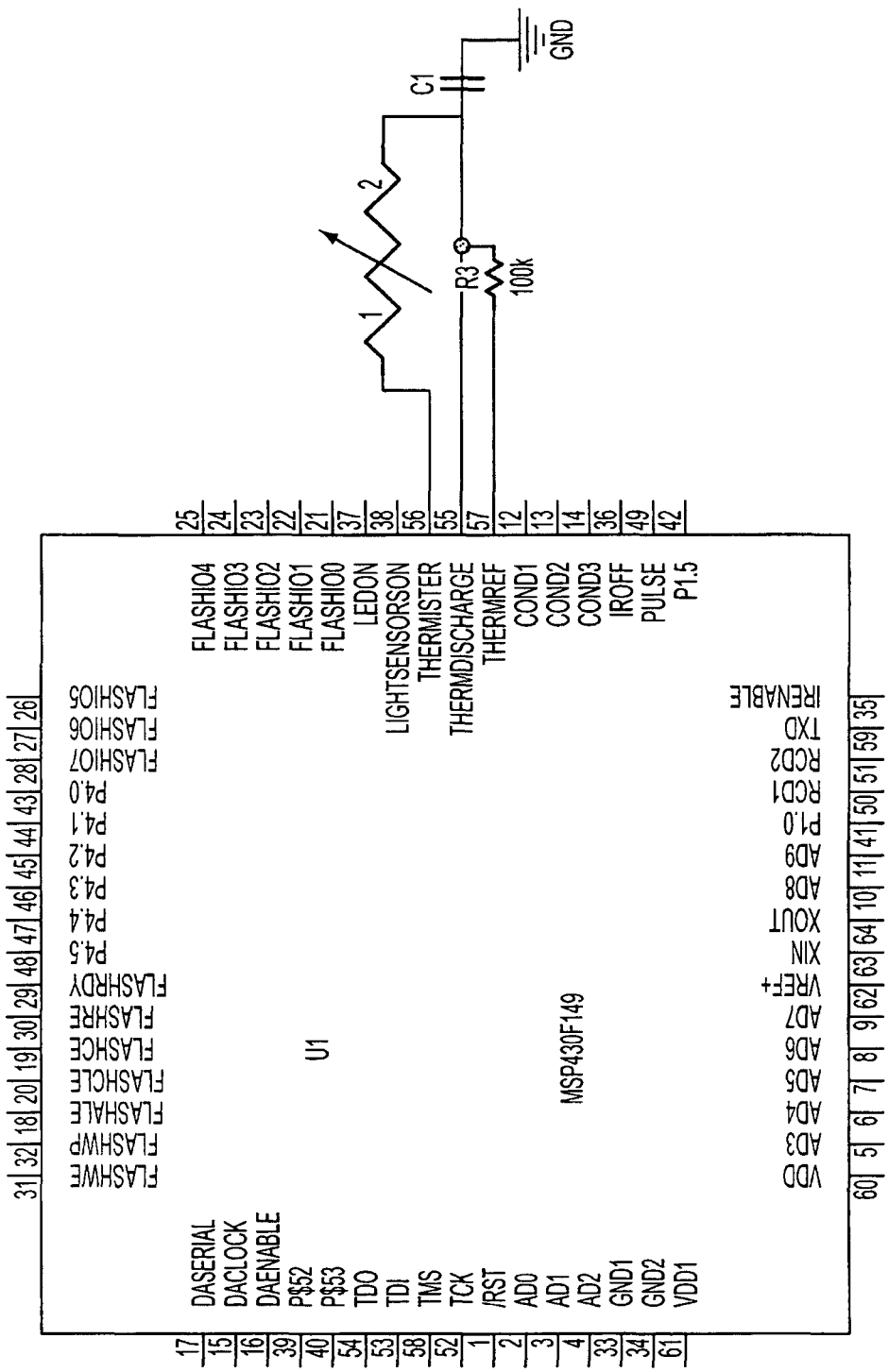
FIG. 11 is a schematic of a temperature sensor.

The temperature sensor is based on a temperature measuring technique described in the literature. It is implemented using a 100K thermister and a 0.1 µF capacitor. The principle of operation can be understood by referring to FIG. 11.

The capacitor is charged through the Thermdischarge pin. This pin is then floated. A software timer is started and the Thermref pin is grounded. The time to discharge C1 though R3 is measured. This is the thermister reference time. Thermref is floated, C1 is again charged through the Thermdischarge pin, and a software timer is started. The time to discharge C1 through the thermister is measured as the thermister time.

A plot of the ratio of thermister/thermister reference vs. temperature is non-linear as expected for a negative temperature coefficient (NTC) thermister. It can be made somewhat linear with a log plot, and this calibration is used for the sensor. More complicated, polynominal fits have been tried for the EMS system but do not produce much higher precision. To provide high accuracy, polynominal fits have been proposed for measuring the temperature in the marine environments.

Figure 12:
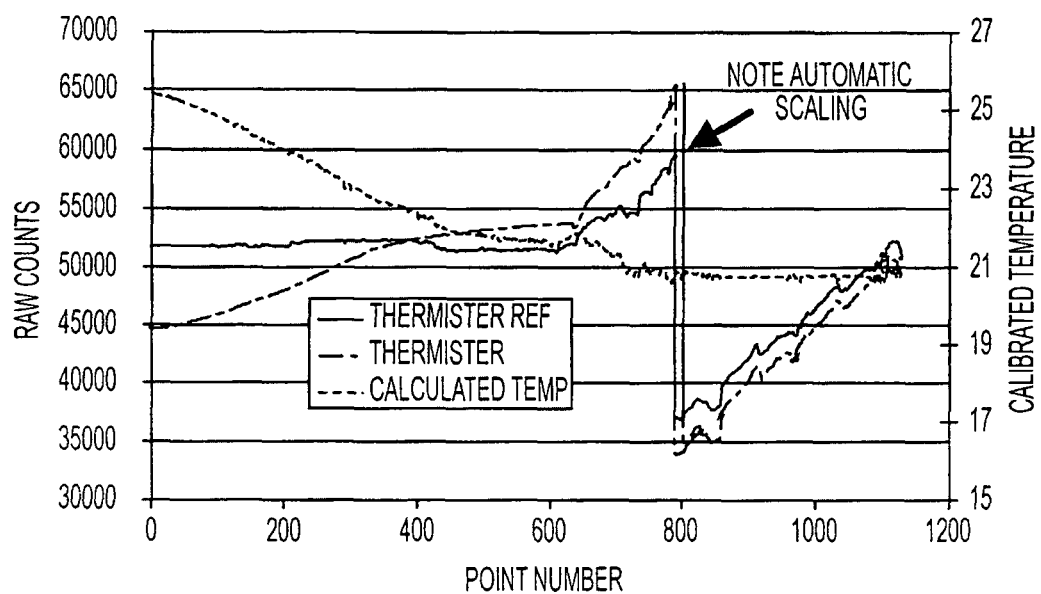
FIG. 12 shows an example of automatic scaling.

Because the resistance of the 100K thermister varies considerably over the 0-50° C. range of interest, an autoranging feature was implemented. The discharge time is inversely related to the discharge resistance. If the timer overflows, because the thermister resistance becomes too high (at lower temperatures as a NTC thermister is used), the timer clock is decreased and the measurement is repeated for both the reference and thermister measurements (see FIG. 12, which is an example of automatic scaling—note that automatic scaling has little effect on the noise of the calculated temperature). Two autoranging levels are necessary within the 0-50° C. temperature range. The resolution of this measurement is <0.05° C. The EMS unit is sensitive enough to measure and record variations in the room air temperature with the cycling of the heating system. However, the absolute accuracy varies because of the drift in R3, which also changes with temperature. Because the EMS unit will be in a water stream, the temperature of R3 will vary with the water temperature. However, the absolute accuracy varies because of the drift in R3, which also changes with temperature (for example of drift, see the thermister reference in FIG. 12). This reference resistor (R3) has a 100 PPM/° C. drift. Other, more-expensive resistors are available with drifts as low as 15 PPM/° C. but their lead-time for purchase is quite long and require bulk purchases. Alternatively, the temperature of the microprocessor (and indirectly R3) is measured and can be used to correct the drift in R3 with ambient temperature. These more complicated schemes were not employed because highly-accurate temperature measurements are not necessary as even a drift of 100 PPM/° C. is only an error of 0.5% over the 50° C. temperature range of interest. In bench testing, the absolute temperature reading appears to be within 1° C. relative to an alcohol thermometer, which was used for the calibration.

Alternatively, a commercial thermister chip could be used. This has the advantage of allowing for a simplified design of the environmental monitoring system. Another advantage of using a commercial thermister chip, is that they are factory calibrated.

Amperometric Measurements

Figure 13:
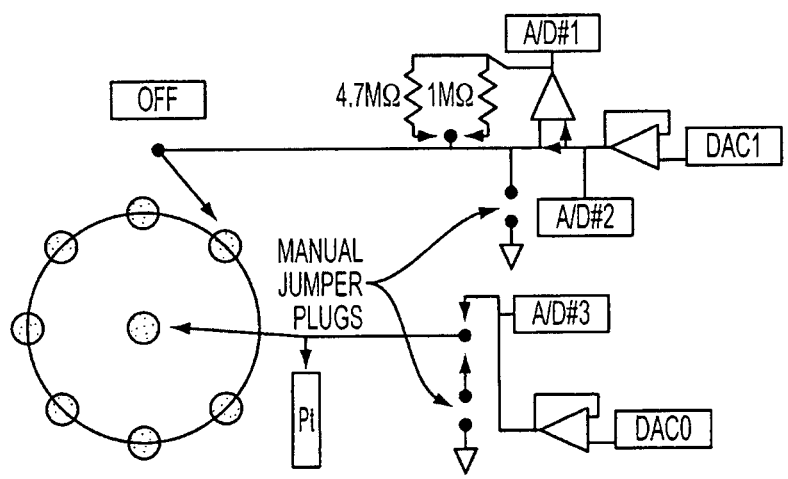
FIG. 13 is a schematic outline of an electrode maker board.

Amperometric measurements rely on current rather than potential. A small, separate card (electrode maker board) was constructed and programmed to allow full control over the potential applied to the working electrodes and selection from a number of working electrodes. The outline of this circuit is shown in FIG. 13. The interface to the on-board microprocessor and its connection to the outside world are not shown. DAC is digital to analog converter, and A/D is analog to digital converter. The circular array has connections to working electrodes, which may be selected under software control. The arrows indicate switches, which also may be changed under software control. Because all the potentials are digitally controlled, any number of ramps or pluses can be generated. This amperometric circuitry can also be incorporated into the environmental monitoring system to generate a single board solution.

The design of the electrode maker board is unique compared to normal amperometric measurement systems as an offset voltage may be applied to the reference electrode. The environmental monitoring system (EMS) allows a single 3V battery to supply the system and yet make measurements over a wide range of voltages. An example of the software programming to allow a ±1.25V scan on working electrode #1, using the Pt electrode as the counter electrode is possible by replacing the 4.7 MΩ resistor in FIG. 13 with a 100 MΩ resistor. In this example, 1250 mV are applied to the current converting operational amplifier through a buffer amplifier. This allows the output of this amplifier to vary from 0 to 2.5V on a single positive power supply.

Figure 14:
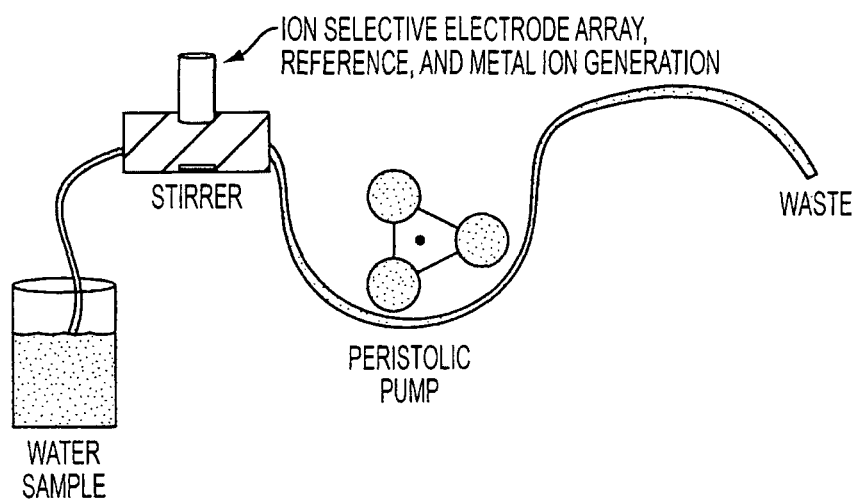
FIG. 14 is a schematic of an automated system for measuring free metals and their binding capacity.
Figure 15:
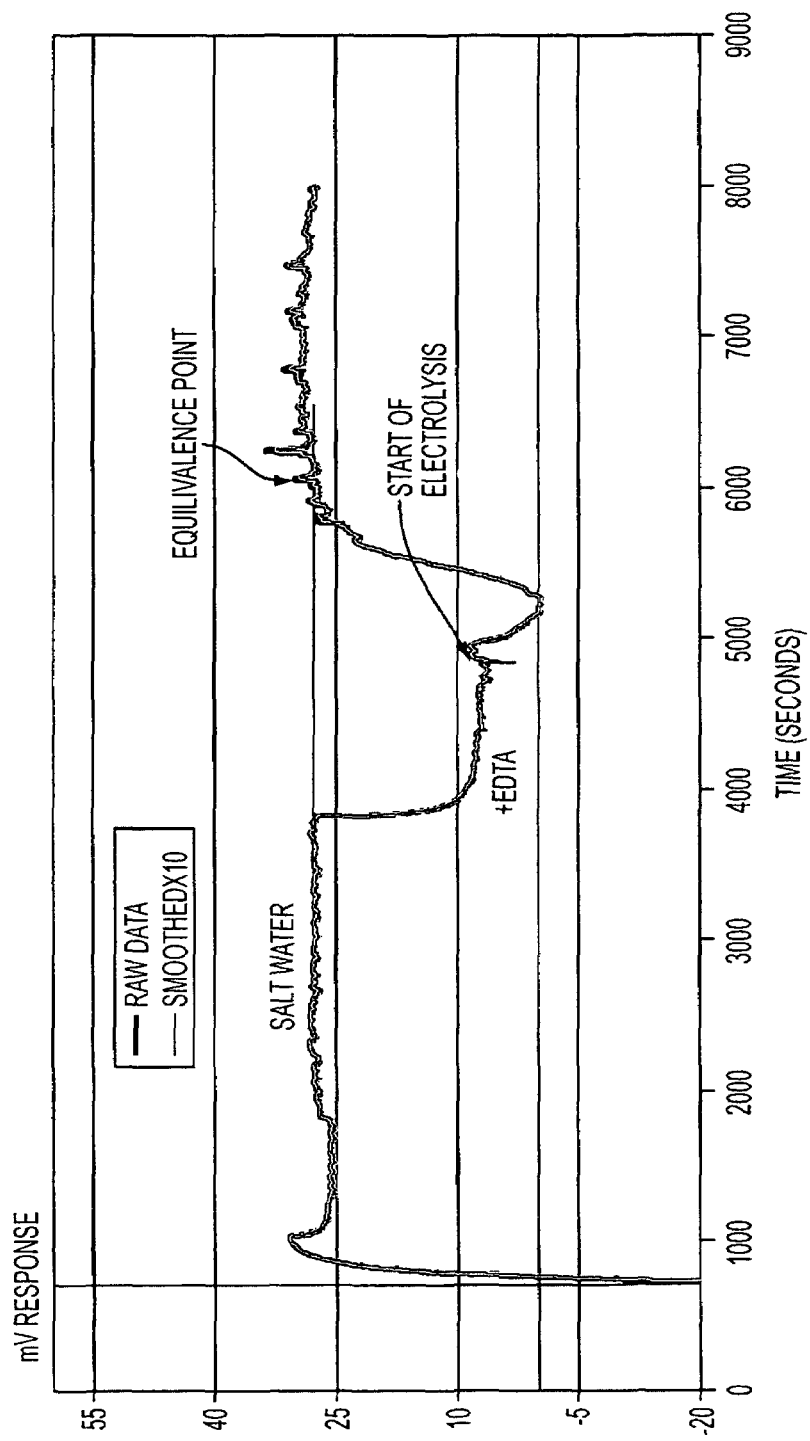
FIG. 15 shows the results from measuring ligand binding in salt-water solutions.

Amperometric measurements and capabilities to generate controlled currents are useful to measure excess binding capability of natural waters. FIG. 14 shows a schematic design of such an instrument using the electro maker board as the current generating device and the EMS as the ion selective electrode monitoring system. FIG. 15 shows an analysis of simulated seawater where a known amount of EDTA was added to mimic the binding capability of natural water. To measure excess binding capability, a water sample is taken and a controlled amount of a specific ion is added. In this case, it can be added automatically by controlled electrolysis of a copper wire (to add copper ions in this example). The total current needed to react an inflection point is proportional to the amount of copper added which is then proportional to the excess binding capacity of that water sample for copper. Because different wire samples may be employed, different ions may be generated in a controlled fashion, on-demand, without solutions being present. This allows such a system to be developed in a miniature package. See: David A. Kidwell, "Measuring Copper in Seawater—An Automated Detection of Copper Binding Capacity Final Report of SERDP SEED 1266," NRL Memorandum Report 6170-03-8729, Dec. 19, 2003, the entire contents of which are incorporated herein by reference.

Software to Calculate Quality of Data

Ion selective electrodes are sensitive to other ions present in the solution. Because a number of ions are being measured, software can be incorporated to take into account the other ions present that interfere with each other and to iteratively remove the interferences. Additionally, conductivity can be used to estimate activity coefficients for higher ionic-strength solutions as ion selective electrode actually measure activity of ions in solution not their concentration.

Ion selective electrodes monitor specific ions whereas the conductivity sensor monitors all ionic species in solution. Because the ion selective electrodes do not measure all ionic species, some ionic materials may be missed. For the majority species, if the calculated conductivity from the ion selective electrodes matches that from the conductivity sensor one can have greater confidence that additional ionic species were not present in substantial concentrations. This is the quality of data index, which is calculated from:

$$QDI = 100 - (|C_{calculated} - C_{measured}|/C_{max})$$

where:

$QDI$=Quality of Data Index (number from 0-100 with 100 best perfect match)

$C_{calculated}$=conductivity from all species calculated from conductivity tables and identified by the ion selective electrodes $C_{measured}$=measured conductivity $C_{max}$=maximum of $C_{measured}$ or $C_{calculated}$ Conductivity varies by species and temperature. Therefore, the calculated conductivity must take the ionic species and temperature into consideration. This can be accomplished through look-up tables or from equations fitted to the look-up tables.

Additionally, the measured (or calculated) conductivity can be used to estimate the activity coefficient needed for accurate calculation of the concentration of ions present. Because the calculated conductivity depends on the measured concentrations and the measured concentrations depend on the conductivity, this can be solved in an iterative fashion or better by using the measured conductivity in the calculations rather than the calculated conductivity.

A program that can be used with the environmental monitoring system uses equations fitted to conductivity data from the literature. A quadratic fit is used rather than a linear fit. The algorithm is as follows:

Start with the ionic response of the various ion selective electrodes to get an approximate value and possible ions present Sum the cations and anions. If not equal assume that sodium or chloride makes-up the remainder. However, report that unknowns are present.

If sodium or chloride is being measured then choose another cation or anion that is not being measured Estimate the conductivity from the sum of the conductivities of each salt. Assume that Kohlrausch's law of independent conductivities applies.

Use Kohlrausch's laws fit with a quadratic equation to estimate conductivity. Kohlrausch used a linear equation, which has a much poorer fit.

Alternatively, use look-up tables as in the Handbook for Chemistry and Physics (CRC Press) and extrapolate between values (this requires at lot of data).

Correct the conductivities from the recorded temperature and the assumed salts present.

Compare calculated conductivity with measured results and report difference. If large flag result.

If result is large error, substitute other cations to minimize error and recalculate. Report assumptions.

If result is still too large, report that negative ions may be present.

pH is critical as H+ can dominate conductivity measurements.

Take into account selectivity coefficients and activity coefficients in estimating the ionic concentrations.

Important if the values are >0.01M in any salt.

For ions such as phosphate that we only measure one form, calculate other forms based on pH and pKa's Current limitations:

If ionic complexation is occurring then BOTH the conductivity measurements and the ISE measurements will be incorrect.

Ionic complexation is ASSUMED to be low at low concentrations. Flag higher concentrations as possibly complexation occurring.

Alternatively:
Instead of fitting Kohrausch's data to a quadratic using sqrt [ ], use activity and fit to a linear curve
Apparent sqrt non-linearity is really due to activity.
May need to use the Stokes-Robinson equation or the Miller modification to determine activities.

NOTES:
Activity only needed if reporting concentrations. Both the conductivity and the ISE voltage vary with activity in a similar manner.
Thus conductivity can cross-check ISE values with knowing the activity.
Back estimate concentration from calculated activities.

The difference in this program is that the conductivity data is separated into individual ions by assuming that for KCl, the conductivity of each ion is half of the total. From this one assumption, all the other individual conductivities may be calculated. Other authors have estimated the negative ion and positive ion conductivities differently and generated self-consistent sets of conductivity data for individual ions. Examples of using the cross-checking ability may be seen in Table 1. The percent agreement is calculated from:

100−((Measured Conductivity−CalculatedCond)/
(Measured conductivity)*100)

Using this method, the values can be much higher or lower than 100; values equal to 100 mean a perfect fit.

being measured. The provided data showed that bicarbonate (as hardness) and sulfate were other major ions present in the water. Adding the average values for these ions into the calculation gave a 127% agreement with the measured values. This higher agreement indicates that either the average values were too high for this particular water sample or the data set in the calculations needed modification.

Likewise, the analysis of Pepsi measured approximately 0.95 mM sodium by two methods—direct measurement and standard addition. The reported value was 4.5 mM. The lower measured value to that on the label is likely due to how Pepsi is bottled. Drinking water is used in the bottling, which varies in quality from source to source and day to day. The label probably reflects the maximum amount of sodium that could be present rather than the actual amount. Because of the varying water sources, printing new labels with actual lot quality would not be cost effective. The low agreement (10%) in conductivity implies that other ions are present (probably bicarbonate from the carbonation).

The "spring water" sample in Table 1 was from a bottled water source and labeled as no sodium. The sample indeed showed no sodium with a sodium ISE and only very low conductivity. This very low conductivity indicates that few other ions are present and this sample is most likely distilled water rather than "spring water" as advertised.

Standards solutions #1-4 are displayed in three ways: (1) The (+) agreement is with the measured positive cation and the chloride concentrations assumed to balance the charge. (2) The (−) is with the measured chloride concentration and

TABLE 1

Examples of cross-checks between ISEs and conductivity.

| Matrix | Concentration of Ions | Measured Concentration | Conductivity (mS) | % Agreement |
|---|---|---|---|---|
| Tap Water | 0.74 mM Na+<br>0.84 mM Cl−<br>0.370 mM Mg2+<br>1.073 mM Ca2+ | 0.84 mM Cl− | 0.370 mM Mg2+ | 18%<br>127%. |
| Pepsi | 4.5 mM Na+ | Direct: 0.95 mM<br>Standard Addition:<br>0.97 mM | 0.887 | 10% |
| "Spring Water" | Sodium Free | No sodium detected | 0.000956 | |
| Standard Solution #1 | 5.000 mM NaCl | 5.007 mM Na+<br>5.032 mM Cl− | 0.5940 | 100.78% (+)<br>101.27% (−)<br>100.64% (program) |
| Standard Solution #2 | 0.09999M KCl | 0.1022M K+<br>0.09889M Cl− | 12.63 | 103.33%<br>100.13%<br>101.19% |
| Standard Solution #3 | 0.05025M CaCl2 | 0.05386M Ca2+<br>0.1018M Cl− | 9.81 | 103.50%<br>98.05%<br>96.85% |
| Standard Solution #4 | 0.04988M MgCl2 | 0.04539M Mg2+<br>0.09417M Cl− | 8.60 | 92.38%<br>95.68%<br>101.28% |
| Standard Solution #5 | 0.489 mM Na+<br>2.23 mM Cl−<br>0.990 mM Ca2+<br>0.243 mM HCO3− | 0.429 mM Na+<br>2.27 mM Cl−<br>0.926 mM Ca2+ | 0.2653 | 91%<br>(with bicarbonate)<br>90.8% w/o<br>bicarbonate |

NOTE:
the conductivity was measured with a commercial conductivity meter from YSI and the values adjusted using standard KCl solutions.

Only ISEs were available for four ions. When measuring tap water the measured ion values were within the range reported by the Washington Sanitary District as average values for tap water. However, the measured and calculated conductivity was only 18% in agreement, indicating that substantial amounts of other ions were present that were not the cation assumed to balance the charge. and (3) The agreement without a reference is the value calculated from the known concentrations. All values agreed well.

The standard solution #5 was a mixture of calcium chloride and sodium bicarbonate. Without considering the bicarbonate concentration, the agreement was poor. Including the bicarbonate concentration the agreement was 91%. By assuming that all the bicarbonate was chloride, a 90.8% agreement could be reached. The agreement by inputting the actual concentrations rather than the measured concentrations was 96%.

From the examples in Table 1, it is proposed that the sensor system compare the measured ions to other orthogonal sensors, such as conductivity, and sound an alarm if agreement is poor or one specific sensor indicates that a toxic species may be present. As is obvious from Table 1, the major species of bicarbonate and sulfate must also be measured for reasonable agreement in surface water systems. One should note that the form of bicarbonate (as bicarbonate or carbonate) depends on pH and both can be calculated from a single ISE sensitive to bicarbonate by knowing the pH. Likewise, the form phosphate is in varies with pH and an ISE measurement sensitive to PO4-2 could additionally measure all form by knowing the pH.

External Communications

Figure 16:
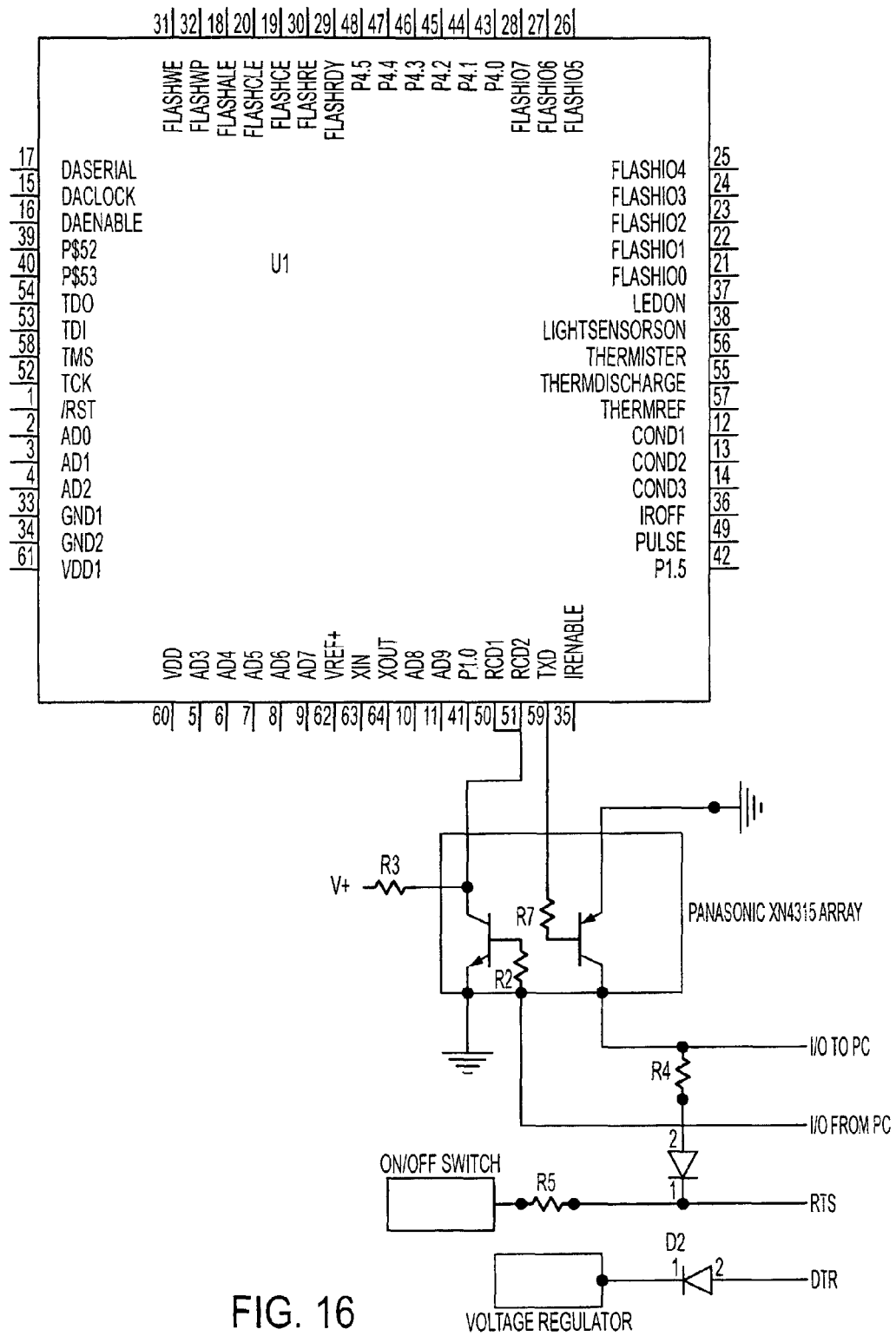
FIG. 16 is a partial schematic of the RS232 port and voltage supply.

The RS232 port is used to both communicate to the PC and power the EMS. For communication, the RS232 specifications call for a voltage change of −12 to +12V to signal the presence of bits. A number of RS232 voltage level converters are available to produce these voltage levels from a single voltage supply. Unfortunately, they all have considerable power consumption. A more simplistic scheme was chosen for voltage level conversion in the EMS. The partial circuit is shown in FIG. 16 along with the power supply from the PC voltages. The voltage from DTR (from the PC) is used to power the device. Because this level can be negative, a protection diode (D2) is in series with this input. Voltage is regulated with a series regulator and filtered with several tantalum capacitors. RTS is used to provide the negative voltage for sending a null to the PC. It is pulled positive (to V+) when bits are sent. Although V+ is nominally 3.3V and does not meet the ±15V RS232 standard, this is sufficient to trigger most RS232 receive ports if the wire length is kept short (<20 feet). RTS is also used to turn on the EMS with a negative voltage being on. D1 is used to prevent power leakage into the EMS when the RTS is off (high state). Communication is at 9600 BAUD. All bit timing and decoding is accomplished using software.

The above description is that of a preferred embodiment of the invention. Various modifications and variations are possible in light of the above teachings. It is therefore to be understood that, within the scope of the appended claims, the invention may be practiced otherwise than as specifically described. Any reference to claim element sin the singular, e.g., using the articles "a," "an," "the," or "said" is not construed as limiting the element to the singular.

What is claimed is:

1. A monitoring device, comprising:
    (a) a cast membrane reference electrode comprising a membrane comprising a hydrophilic polymer and a hydrophobic polymer;
    (b) at least one sensing electrode that measures a specific parameter relating to water quality, wherein there is electrical contact between the reference electrode and the at least one sensing electrode;
    (c) an indicator for said electrical contact; and
    (d) optionally, an absorbance sensor, a fluorescence sensor, a conductivity sensor, a temperature sensor, or any combination thereof;
    wherein said monitoring device weighs less than one pound, is less than four inches in width, and is less than six inches in length.

2. The monitoring device of claim 1, wherein the data collected can be stored within the monitoring device.

3. The monitoring device of claim 1, wherein the monitoring device can communicate with another device through a direct connection, an IR connection, radio waves, or any combination thereof.

4. A monitoring system, comprising:
    (a) a cast membrane reference electrode comprising a membrane comprising a hydrophilic polymer and a hydrophobic polymer;
    (b) at least one sensing electrode that measures a specific parameter relating to water quality, wherein there is electrical contact between the reference electrode and the at least one sensing electrode;
    (c) an indicator for said electrical contact; and
    (d) optionally, an absorbance sensor, a fluorescence sensor, a conductivity sensor, a temperature sensor, or any combination thereof;
    wherein data obtained by a sensing electrode or an optional sensor from (d) can be compared with data obtained by a different sensing electrode or optional sensor from (d) that measures a similar aspect of the water, thereby improving the effectiveness of the monitoring system in detecting a water quality concern;
    wherein said monitoring device weighs less than one pound, is less than four inches in width, and is less than six inches in length.

5. The monitoring device of claim 4 wherein the monitoring system has a conductivity sensor and uses a computer program to compare conductivity calculated from data obtained by a sensing electrode with conductivity data obtained by the conductivity sensor.

6. The monitoring system of claim 4, wherein the data collected can be stored within the monitoring system.

7. The monitoring system of claim 4, wherein the monitoring system can communicate with another device through a direct connection, an IR connection, radio waves, or any combination thereof.

\* \* \* \* \*